United States Patent [19]

Kuroda et al.

[11] Patent Number: 5,974,860
[45] Date of Patent: *Nov. 2, 1999

[54] OIL DETECTING SYSTEM

[75] Inventors: Hidehiko Kuroda; Naruhiko Mukai; Teturo Aikawa; Kunihiko Yokoyama, all of Yokohama; Masahiko Kuroki; Takashi Kokubo, both of Kawasaki, all of Japan

[73] Assignee: Kabushiki Kaisha Toshiba, Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/853,949

[22] Filed: May 9, 1997

[30] Foreign Application Priority Data

May 9, 1996 [JP] Japan ................................ 8-114679

[51] Int. Cl.$^6$ .............................. G01M 3/40; F21Y 09/06
[52] U.S. Cl. ........................... 73/40; 73/40.5 R; 250/301; 250/492.1; 356/318
[58] Field of Search ................................... 73/40, 40.5 R; 250/301, 484.1, 459.1, 492.1; 356/318, 72

[56] References Cited

U.S. PATENT DOCUMENTS

| 2,096,099 | 10/1937 | Gaugler | 73/51 |
|---|---|---|---|
| 3,483,736 | 12/1969 | Anderson | 73/40.7 |
| 3,572,085 | 3/1971 | Packo | 73/40.5 |
| 3,770,640 | 11/1973 | Barlett | 252/68 |
| 3,980,882 | 9/1976 | Carr-Brion et al. | 250/272 |
| 4,147,431 | 4/1979 | Mann | 356/72 |
| 4,200,801 | 4/1980 | Schuresko | 250/458 |
| 4,724,217 | 2/1988 | Miller | 436/82 |
| 4,758,366 | 7/1988 | Parekh | 252/68 |
| 4,897,551 | 1/1990 | Gersh et al. | 250/461.1 |
| 5,001,353 | 3/1991 | Odake et al. | 250/461.1 |
| 5,022,757 | 6/1991 | Modell | 356/318 |
| 5,119,463 | 6/1992 | Vurek et al. | 385/129 |
| 5,161,408 | 11/1992 | McRae et al. | 73/40.7 |
| 5,357,782 | 10/1994 | Henry | 73/40.7 |
| 5,411,682 | 5/1995 | Nagashima | 264/36 |
| 5,440,919 | 8/1995 | Cooper | 73/40.7 |
| 5,449,918 | 9/1995 | Krull et al. | 250/458.1 |

FOREIGN PATENT DOCUMENTS 6-129987  5/1994  Japan .

*Primary Examiner*—Hezron Williams
*Assistant Examiner*—J. David Wiggins
*Attorney, Agent, or Firm*—Oblon, Spivak, McClelland, Maier & Neustadt, P.C.

[57] ABSTRACT

An oil detecting system for detecting a leakage oil by optical fluorescence measurement means even in the presence of external fluorescent light, for example, from parts and equipments of a vehicle and a plant comprises an irradiation apparatus for irradiating a light including an absorption wavelength of an oil to be detected and exciting molecules of the oil to make the oil fluoresce, a wavelength selection apparatus operatively connected to the irradiation apparatus and adapted to select a fluorescence wavelength of the leakage oil fluoresced by the irradiation apparatus, and an observation apparatus for detecting the fluorescence of the leakage oil and selecting only a period of observing fluorescing of the leakage oil over substantially the same time period that the leakage oil fluoresces light. A processing apparatus may be further provided so as to be operatively connected to the observation apparatus and adapted to process an image or a signal from the observation apparatus.

27 Claims, 24 Drawing Sheets

FLUORESCENCE SPECTRUM MEASUREMENT RESULT (MHC OIL)

OIL DETECTING SYSTEM

BACKGROUND OF THE INVENTION

The present invention relates to an oil detecting system for detecting oil leakage from equipments or parts constituting a plant or a vehicle, particularly, capable of computing or operating a leakage film thickness, leakage area and leakage quantity and specifying the type of leaking oil and oil leaking portion.

In a known art, there have been provided various methods for detecting oil leakage from equipments or units in a plant, including a method of visually observing oil leakage by workers, a method of locating a dish-shaped oil pan to a portion at which an oil leakage is expected to drop in the oil pan, a method of detecting oil leakage by utilizing a change in capacitance or resistance due to oil infiltration collected in an oil pit, and a method of detecting an oil leakage by detecting a change in transmissive light intensity by utilizing an optical fiber cable system.

Furthermore, an oil leakage from an engine of a vehicle under manufacturing is detected by a method of irradiating ultraviolet-rays on a leakage oil to thereby detect fluorescence of the oil. In this method, in order to external disturbance such as an influence of a fluorescent lamp, it is necessary to dispose the engine and the oil leakage detecting device in a dark room and to dispose a visual light cut filter in front of a black light (ultraviolet lamp) to prevent fluorescence wavelength of the oil to be detected from being overlapped at a time of irradiating the ultraviolet rays to thereby irradiate only the ultraviolet ray area. The fluorescence of the oil through the ultraviolet irradiation is amplified by an image intensifier and photographed by a CCD camera.

In the above various oil detecting methods in the known art, the visual method includes a problem such that the workers cannot be always visually inspect every position and inspecting ability of the workers differs from respective workers. It is also difficult for the workers to always continue the visual observation.

In the method of detecting oil leakage through accumulation of the oil in the oil pan or oil pit, it is difficult to detect the oil leakage in an early stage of the leakage and also difficult to determine the oil leaking portion and it is also necessary to ensure a position of the location of the oil pan or oil pit.

In the method of utilizing the optical fiber cables, it is necessary for the leaking oil to contact the fiber cables and, accordingly, it is difficult to exactly specify the oil leaking portion and oil leaking condition.

Still furthermore, in the oil leakage detection from the parts of a vehicle such as engine, it is necessary to specifically set a dark room or portion, providing a troublesome problem. Moreover, a fluorescent luminescence is caused to the engine parts, for example, formed of resin material, due to the irradiation of the ultraviolet rays, which may be erroneously detected as oil leakage, and since a fluorescence intensity is very weak, it is necessary to add a fluorescence agent to increase the fluorescence intensity for a certain oil. It is also difficult to discriminate the kind of the leaking oil.

Furthermore, the prior art for measuring an oil film thickness using the fluorescent method includes a method and an apparatus for measuring an oil quantity on the surface of a steel plate under production, for example, disclosed in Japanese Patent Laid-open Publication No. HEI 4-18763. A laser beam is applied to an oil-coated steel plate or the surface of the steel plate to make the oil fluoresce. Then, by measuring the fluorescent spectrum intensity of a component contained only in an oil in the fluorescence emitted from the surface of the steel plate, it is possible to obtain the thickness of a coated oil film because the fluorescence intensity is proportional to the film thickness. However, when actually performing oil film measurement, the measured value of a fluorescence intensity is influenced by the surface roughness of a substrate steel plate or a steel plate in coil. Therefore, an analytical curve showing the relation between fluorescence intensity and coated oil quantity for each surface roughness is previously prepared to obtain a coated oil quantity from the analytical curve and a fluorescence-intensity measurement result. When a coated area has been already known, it is possible to easily estimate a film thickness in accordance with the coated oil quantity.

The art for measuring an oil leaking area includes an oil-cell damage decision apparatus for citrus and the like disclosed, for example, in Japanese Patent Laid-open Publication No. HEI 6-129987. The apparatus and the citrus to be inspected are put in a dark room in order to prevent the influence of a disturbance due to a fluorescent lamp or the like and the surface of the citrus is irradiated with ultraviolet ray or light to make a damaged portion of oil cells fluoresce. Then, the fluorescent area of the damaged portion is obtained by selecting a spectrum region with a high intensity in the fluorescence by a filter, observing the region by a high-sensitivity camera or light detection sensor, and applying image processing or signal processing to the region.

Moreover, if a high-pressure hydraulic oil leaks due to a very-small damaged portion on a unit used for a plant, the oil spouts at a high pressure and, hence, the oil may scatter in a wide area in the form of fine particles. A visual inspection of units through a patrol of a worker, an oil sensor whose capacitances or resistances are changed due to oil contact, and an optical-fiber sensor whose refraction factors are changed are known technique for detecting the foggy leakage oil.

Furthermore, a method for detecting leakage of an oil in accordance with the difference of reflectance between water and oil by irradiating the water surface with a laser beam and detecting the reflected light is known as a technique for monitoring the oil leaking from a drain outlet of a plant or building.

However, in the prior art techniques mentioned above, when applying the oil film measuring apparatus disclosed in Japanese Patent Laid-open Publication No. HEI 4-18763 or the oil-cell decision apparatus disclosed in Japanese Patent Laid-open Publication No. HEI 6-129987 to the detection of oil leaking from a unit in a plant or a part of a vehicle or the like, the following problems occur.

Firstly, the apparatus cannot be used under a bright environment where disturbance light such as sunlight or illumination is present. This is because the number of disturbances increases and accordingly, the disturbance light ratio S/N to the fluorescence intensity of an oil to be detected is decreased.

Secondly, the film thickness measuring accuracy is lowered due to aged deterioration of an irradiation apparatus. The fluorescence intensity of the oil depends on the irradiation intensity of an irradiation apparatus in addition to a film thickness. Therefore, as the irradiation apparatus is deteriorated and the irradiation intensity is degraded, the intensity of the fluorescence emitted from an oil is weakened even if the film thickness is not changed. As a result, because an oil detector computes a film thickness in accordance with a fluorescence intensity, it decides the film thickness more thinly.

In addition to the above problems, the conventional oil detection technique using the fluorescence method cannot compute the film thickness distribution, area, or quantity of an oil leaking from a unit in a plant or a part of a vehicle or the like or specify the kind or type of the oil.

In the case of the visual inspection of units in a plant, it is not preferable that an inspector patrols in the atmosphere of foggy leakage oil from the viewpoint of safety. Under a state in which the field of view may be impaired like the above situation, it is difficult to specify a leakage portion.

Moreover, a capacitance- or resistance-type sensor has only a sensitivity for detecting the amount of oil leaking from a unit and dropped. It is difficult to detect foggy oil in which the oil becomes foggy fine particles and scatters in a wide area because the amount of oil to be detected by an oil sensor is very small.

An optical-fiber sensor decides a portion where oil adheres to a fiber as a leakage portion. In the case of the detection by the optical-fiber sensor, there is a problem that it is difficult to specify a leakage portion because foggy leakage oil scatters in a wide area and adheres to a fiber widely.

The reflection-type oil detection technique for detecting whether oil leaks from a drain outlet of a plant or building in accordance with the difference of reflectance between water and oil detects leakage oil by using the fact that the reflectance of thin-film oil floating on water surface is larger than that of water. Therefore, the reflection-type oil detection technique provides a problem that a substance with a reflectance larger than that of water may be detected other than oil. Moreover, the reflection-type oil detection technique also provides the problem that it is impossible to obtain the thickness, leakage area, quantity, and type of an leaking oil.

SUMMARY OF THE INVENTION

An object of the present invention to substantially eliminate defects or drawbacks encountered in the prior art described above and to provide an oil detecting system capable of detecting the oil leakage from a unit or equipment in a plant and a part of a vehicle, foggy oil leaking in the form of foggy fine particles, and thin-film oil floating on water surface, decreasing the frequency of erroneous detection due to the restriction of a detection plate or detection atmosphere, disturbance such as sunlight or fluorescent lamp, or deterioration of an irradiation apparatus and capable of specifying a leakage area, film thickness and its distribution, quantity, type, and leakage portion of the leakage oil.

This and other objects can be achieved according to the present invention by providing, in one aspect, an great oil detecting system for detecting a leakage oil, for example, from parts and equipments of a vehicle and a plant comprising:

an irradiation apparatus for irradiating a light including an absorption wavelength of an oil to be detected and exciting molecules of the oil to make the oil fluoresce;

a wavelength selection apparatus operatively connected to the irradiation apparatus and adapted to select a fluorescence wavelength of the leakage oil fluoresced by the irradiation apparatus; and an observation apparatus operatively connected to the wavelength selection apparatus and adapted to selectively detect the fluorescence of the leakage oil.

In the preferred embodiments of this aspect, the irradiation apparatus comprises a pulse laser serving as a pulse-beam irradiation apparatus, and the wavelength selection apparatus comprises a band-pass filter.

The observation apparatus comprises an image intensifier provided with fast-shutter function and image-intensifying function. The detecting system may further comprises a processing apparatus operatively connected to the observation apparatus and adapted to process an image or a signal from the observation apparatus.

The irradiation apparatus may comprises a pulse-flash lamp.

In another aspect of the present invention, there is also provided an oil detecting system for detecting an oil leakage, for example, from parts and equipments of a vehicle and a plant comprising:

an irradiation apparatus for irradiating an oil to be detected with a pulse beam including an absorption wavelength of a leakage oil and exciting molecules constituting the oil to make the oil fluoresce;

a wavelength selection apparatus operatively connected to the irradiation apparatus and adapted to select a fluorescence wavelength of the oil excited by the irradiation apparatus;

an observation apparatus for detecting and observing the fluorescence of the oil by selecting a period of fluorescing the oil; and a processing apparatus operatively connected to the irradiation apparatus and the observation apparatus for performing image- or signal-processing to an output of the observation apparatus.

In the preferred embodiments of this aspect, the irradiation apparatus comprises a pulse beam source and a wavelength selection device having a curved surface so as to emit an irradiation beam with a purposed wavelength in any direction.

The observation apparatus is provided with a gate function and includes a light detection device for observing fluorescence of the oil and the processing apparatus includes a signal integration device for integrating detection signals of the leakage oil detected by the light detection device. The light detection device may be a photomultiplier or an avalanche photodiode.

The observation apparatus comprises an image intensifying tube provided with fast shutter function and image intensifying function and the processing apparatus includes an image integrating processor for integrating oil fluorescence detection images detected by the image intensifying tube.

The processing apparatus includes an oil film computing device for computing a film thickness of the leakage oil, and the film thickness computing device calculates the oil film thickness in accordance with the fluorescence intensity of the oil observed by the observation apparatus. The film thickness computing device performs an integration processing detection signals of the leakage oil up to a constant value and assumes the oil film thickness in accordance with an integrated number of the integration processings.

The irradiation apparatus includes an irradiation wavelength selection device adapted to adjust a film thickness range to be measured by changing an irradiation wavelength of the light beam from the irradiation apparatus, and the irradiation apparatus may further include a light-source deterioration correction device for correcting a film-thickness measurement accuracy by measuring irradiation intensity of the pulse beam.

The processing apparatus includes a film thickness distribution computing device for obtaining a fluorescence intensity distribution by correcting the fluorescence intensity of a detection image in accordance with an information of a distance from an object to be monitored to the observation apparatus and computing the film thickness distribution of the oil in accordance with the fluorescence intensity distribution.

The observation apparatus includes an image intensifying tube provided with a fast shutter function and an image intensifying function, and the processing apparatus includes an oil quantity computing device for obtaining an oil leakage quantity by extracting a fluorescent region of the oil from a detection image and using the fluorescent region and a film thickness computing result by the film-thickness computing device. The observation apparatus may include an image intensifying tube provided with a fast shutter function and an image intensifying function, and the processing apparatus includes an oil leakage portion specifying device for specifying an oil leakage portion in accordance with a detection image of the oil scattered in form of foggy fine particles.

The irradiation apparatus includes an irradiation head for irradiating the pulse beam to a monitoring area and a reflecting means attached to a front portion of the irradiation head with a predetermined distance for reflecting the irradiation beam from the irradiation apparatus.

The observation apparatus includes an oil-type discrimination device for observing the oil by using more than two kinds of observation wavelength and discriminating a type of the oil in accordance with a fluorescence intensity ratio of the observed two kinds of the observation wavelength.

According to the structures and characters of the embodiments of the present invention described above, the following functions and advantageous effects will be achieved.

In a general aspect, there is provided an oil detecting system for detecting a leakage oil from parts and equipments of a vehicle and a plant by optical fluorescence measurement means even in the presence of external fluorescent light, the system comprising an irradiation apparatus for irradiating a light including an absorption wavelength of an oil to be detected and exciting molecules of the oil to make the oil fluoresce, a wavelength selection apparatus operatively connected to the irradiation apparatus and adapted to select a fluorescing wavelength of the leakage oil fluoresced by the irradiation apparatus, and an observation apparatus for detecting the fluorescence of the leakage oil and selecting only a period of observing fluorescing of the leakage oil over substantially the same time period that the leakage oil fluoresces light. Accordingly, the leakage of oil can be precisely detected even in a fine quantity thereof, and such detection can be done even in an existence of a disturbance such as fluorescent light, which eliminates the restriction on the location of the detecting system and enables to perform an early detection and leakage position discrimination, as well as discrimination of the kind or type of the leakage oil.

The processing apparatus may be also provided to deal with the information of the leakage oil from the observation apparatus.

In the preferred embodiment, by using the pulse-laser apparatus, the oil leakage can be detected with high sensitivity. Any disturbance can be effectively prevented by providing the band-pass filter as the wavelength selection device.

Furthermore, by using the image intensifying tube, the leakage oil can be observed through an image picture or display even in the fine quantity of the leaking oil.

According to the other aspects of the present invention, the following functions and advantageous effects can be further achieved.

It is possible to excite an oil to be detected and make the oil luminesce by using an irradiation apparatus capable of emitting a pulse beam including the absorption wavelength of the oil. It is possible to select and observe the luminescence wavelength and luminous period of the oil by using a wavelength selection device for selecting the fluorescence wavelength of the oil and detecting the oil by an observation apparatus for selecting and observing the luminous time of the oil and selectively detect the feeble fluorescence of the oil to be detected out of the disturbance light such as luminescence of various types of units and substances or fluorescent lamp. Moreover, by applying signal or image processing to a detection result by a processing apparatus, it is possible to improve the detection sensitivity, eliminate the restriction of a detection plate or detection atmosphere, decrease the frequency of erroneous detection due to the disturbance such as a fluorescent lamp or due to deterioration of an irradiation apparatus, and specify an oil leakage area, oil film thickness and its distribution, and leakage quantity of an oil, and the type and leakage portion of the oil.

According to this invention, by constituting the irradiation apparatus with the pulse beam source and the wavelength selection device formed into a curved surface, it is possible to make a pulse beam emitted from a point light source enter the wavelength selection device always vertically to the device, prevent a wavelength selected by the wavelength selection device from changing due to the incident angle of the pulse beam, and using the apparatus as an irradiation apparatus for emitting a purposed wavelength in any direction.

According to this invention, by integrating detection signals of the observation apparatus in a certain period by the processing apparatus and deciding the oil leakage in accordance with the processed signals, it is possible to decrease the frequency of erroneous detection because the presence or absence of oil leakage is decided in accordance with the processed signals in a certain period even if a high-intensity temporally-random disturbance with a luminescence wavelength close to the fluorescence wavelength of an oil occurs nearby a monitoring point.

According to this invention, by integrating detection images of the observation apparatus in a certain period and deciding oil leakage in accordance with the processed images, it is possible to decrease the frequency of erroneous detection because oil leakage is decided in accordance with the processed images in a certain period even if a high-intensity temporally-random disturbance with a luminescence wavelength close to the fluorescence waveform of an oil occurs in a monitoring region.

According to this invention, it is possible to compute the film thickness of an oil by using the fact that the detection intensity of an observation apparatus depends on the film thickness of the oil and thereby, performing signal or image processing by the processing apparatus.

According to this invention, by selecting an irradiation wavelength under a condition in which an irradiation intensity corresponds to a fluorescence intensity without being saturated at a film thickness to be measured in the irradiation apparatus, it is possible to adjust a measurable film-thickness range when obtaining the film thickness of an oil by using the fact that the film thickness corresponds to the fluorescence intensity.

According to this invention, by measuring the irradiation intensity of the irradiation apparatus and correcting the detection result of the processing apparatus, it is possible to improve the accuracy of the light-source deterioration prevention unit degraded due to degradation of the fluorescence intensity of an oil because of degradation of the irradiation intensity.

According to this invention, by measuring an irradiation intensity in an irradiation apparatus to obtain a deterioration rate=(reference irradiation intensity)/(measured irradiation intensity) and computing the deterioration rate for the film thickness of an oil obtained by a processor, it is possible to improve a film-thickness measuring accuracy degraded due to degradation of an irradiation intensity.

According to this invention, because the film thickness corresponds to the fluorescence intensity, it is possible to obtain the film thickness of the oil in accordance with the observed fluorescence intensity by the processing apparatus.

According to this invention, it is possible to obtain the film thickness of the oil in accordance with (oil leakage decision film thickness)/(integration frequency) by recording the fluorescence intensity of an oil-leakage decision film thickness for deciding oil leakage in the processing apparatus, integrating detection signals of an observation apparatus until the detection signals have the fluorescence intensity to obtain the integration frequency, and using the fact that the film thickness is proportional to the fluorescence intensity.

According to this invention, it is possible to obtain the film thickness distribution of the oil because of the fact that the film thickness corresponds to the fluorescence intensity when obtaining the fluorescence intensity distribution by correcting the fluorescence intensity of the detection image in accordance with the distance relation between the monitoring object and the oil detector.

According to this invention, it is possible to obtain an oil leakage quantity by extracting the fluorescent region of the oil from the detection image and computing the film thickness distribution computed by the film-thickness computing apparatus for the extracted fluorescent region.

According to this invention, it is possible to discriminate the type of oil in accordance with the observation wavelength of the observation apparatus and image processing by the processor and discriminate the type of leakage oil.

According to this invention, it is possible to discriminate the type of oil because when the ratio between fluorescence intensities of the oil is obtained by observing the oil with two or more types of observation wavelengths, the fluorescence intensity ratio serves as a value peculiar to the type of the oil.

According to this invention, by setting the reflector for reflecting the fluorescence of the oil to the bottom of the drain outlet of the plant or building, it is possible to observe the fluorescence reflected by the reflector in addition to the fluorescence emitted from the oil and improve the detection sensitivity.

According to this invention, it is possible to specify an oil leakage portion of a unit by comparing the detection image of the leakage oil with a detection image of the leakage oil a certain time later and, thereby, computing the moving direction of each foggy oil particle and following up the source from which the foggy oil particle is moved.

The nature and further characteristic features of the present invention will be made clear from the following descriptions of the preferred embodiment made with reference to the accompanying drawings.

DESCRIPTION OF THE PREFERRED EMBODIMENTS

The first embodiment of the present invention is described hereunder with reference to FIGS. 1 to 18. The oil detecting system is adapted to detect leakage oil of various types of units in a thermal power plant.

Figure 1:
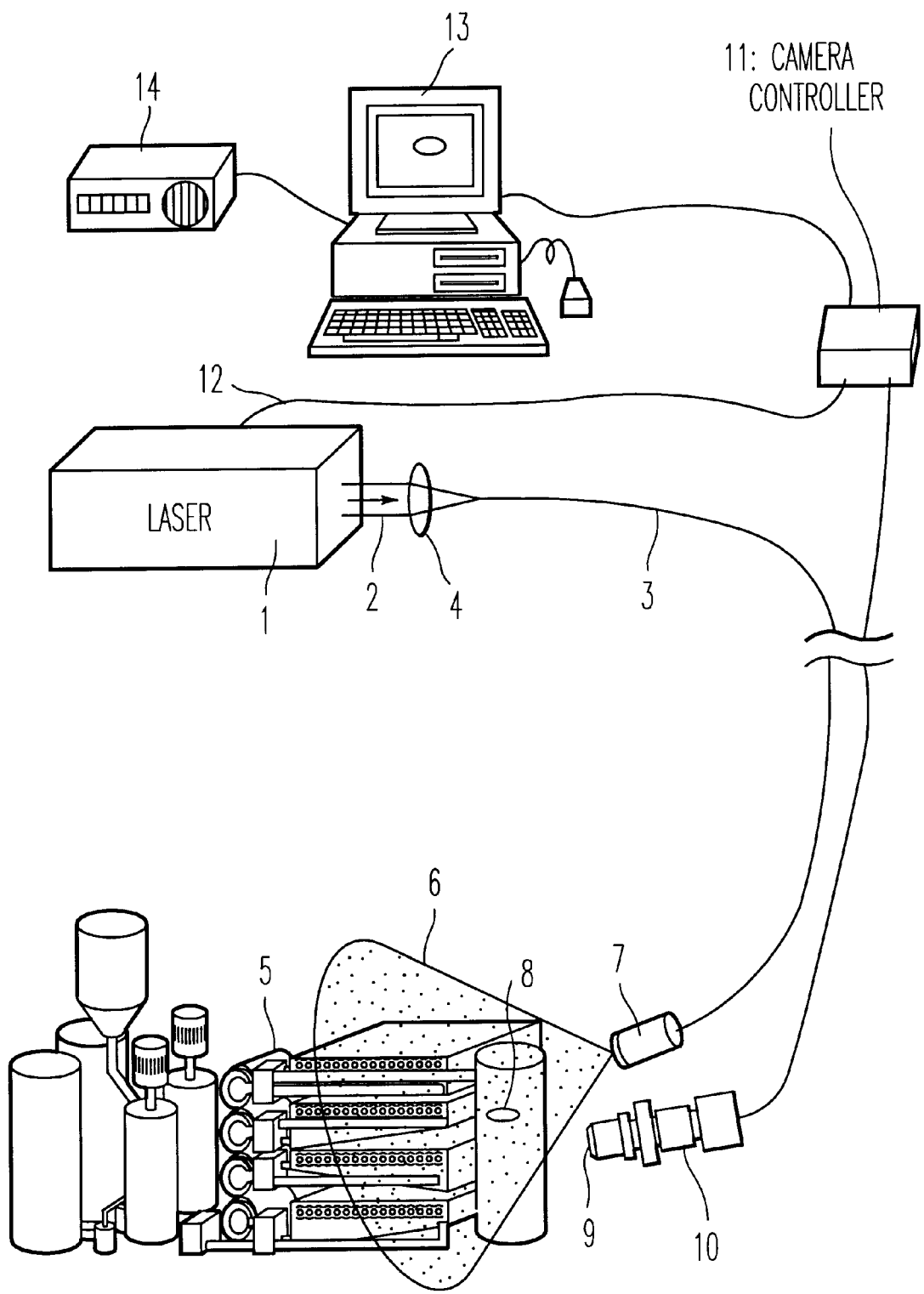
FIG. 1 is a view showing a structural arrangement of an oil detecting system according to a first embodiment of the present invention.

The oil detecting system of the first embodiment shown in FIG. 1 roughly comprises a light irradiation apparatus, an observation apparatus and a signal processing apparatus. The light irradiation apparatus comprises a pulse laser 1 serving as a pulse-beam irradiation apparatus, a lens 4 for introducing a pulse laser beam 2 emitted from the pulse laser 1 into an optical fiber cable 3, and a lens-provided irradiation head 7 for applying the pulse laser beam 2 transmitted up to the vicinity of a monitoring region by the optical fiber cable 3 to a monitoring region 6 having a purposed area on a unit 5 whose leakage oil is detected.

The observation apparatus comprises a wavelength selection device 9 for selecting only the fluorescence emitted from leakage oil 8 produced in the monitoring region 6 through wavelength separation, an image sensor 10 with a fast-shutter function serving as a photodetector capable of selecting and detecting only the period in which the fluorescence is emitted from the leakage oil 8 or the time width of the pulse laser beam 2, and a camera controller 11 for controlling the fast-shutter-provided image sensor 10.

The pulse laser 1 and the camera controller 11 are connected each other by a synchronizing signal line 12 so that operations can be performed by synchronizing the irradiation timing of the pulse laser beam 2 with the observation by the fast-shutter-provided image sensor 10.

The signal processing apparatus comprises a computer 13 for inputting an image signal from the camera controller 11 and an alarm 14 connected to the computer 13. In the case of the pulse laser 1, an optimum one is selected in accordance with the absorption spectrum and the fluorescence emission time of the leakage oil 8.

A thermal power plant mainly uses the following five types of oils: steam turbine oil (S/T oil), gas turbine oil (G/T oil), mechanical hydraulic oil (MHC oil), electrical hydraulic oil (EHC oil), and a mixed oil obtained by mixing the above oils at optional rates. These oils have a rate of absorption in a range of a wavelength of approximately 190 to 360 nm as shown by the absorption-spectrum measurement data in FIGS. 2, 3, 4, 5 and 6, respectively. Therefore, the pulse laser 1 must have an oscillation output in a range of 190 to 360 nm.

Moreover, the luminous periods of leakage oils of steam turbine oil, gas turbine oil, mechanical hydraulic oil, electrical hydraulic oil, and mixed (mixture) oil are attenuated within approximately 500 ns as shown in FIGS. 7, 8, 9, 10 and 11. Therefore, to increase a signal-to-noise ratio (S/N ratio), it is more advantageous that the time width of the pulse laser beam 2 is much shorter than the luminous period of an oil.

As a laser capable of achieving the above mentioned functions, it is possible to use the third to fourth harmonic beams of an excimer laser such as a krypton-chloride laser, krypton-fluoride laser, xenon-chloride layer, or xenon-fluoride laser or a pulse solid-state laser such as a neodymium YAG laser, neodymium glass laser, neodymium YLF laser, or neodymium $YV_4$ laser, the second to third harmonic beams of a ruby laser, or the second to third harmonic beams of a wavelength variable laser such as a titanium-sapphire laser, pigment laser, or alexandrite laser.

The data of this embodiment is obtained from a case of using the fourth harmonic of a Q-switch operating neodymium YAG laser wit an output-beam pulse width of 5 ns and an output-beam wavelength of 266 nm for the pulse laser 1.

The optical fiber cable 3 can use any type of a cable as long as it is able to pass the pulse laser beam 2. In the case of this embodiment, an optical fiber having a quartz core is used. Moreover, it is preferable to use a wavelength selection device capable of selectively passing emission spectrums from the leakage oil 8 as the wavelength selection device 9.

Emission spectrums obtained by applying rays with a wavelength of 266 nm to five types of oils used for a thermal power plant are shown in FIGS. 12, 13, 14, 15 and 16. It is necessary to properly select a transmission wavelength of the wavelength selection device 9 in accordance with the emission spectrum of each purposed oil or the disturbance light condition of a fluorescent lamp, sunlight, or incandescent lamp.

This embodiment uses a dielectric multilayer filter serving as a band-pass filter whose transmission wavelength ranges between 290 and 350 nm as the wavelength selection device 9. Moreover, it is possible to use a colored glass filter or a filter using the dispersion due to a grating as the wavelength selection device 9.

The fast-shutter-provided image sensor 10 must have a sensitivity for a light wavelength transmitted through the wavelength selection device 9 and have a shutter function in a range from the approximate luminous period of the leakage oil 8 to the period in which the influence of disturbance light of a fluorescent lamp, sunlight, or incandescent lamp can be avoided, that is, in a range from approximate 100 ns to approximate 70 $\mu$s for five types of oils used for a thermal power plant.

As the above type of sensor, it is possible to use a CCD image pickup device provided with an image intensifier having a gate function, SIT camera, streak camera, television camber provided with a fast-shutter function, or still camera. This embodiment uses a CCD image pickup device combined with an ultraviolet-ray transmission camera lens and an image intensifier having the minimum shutter time of 100 ns as the fast-shutter-provided image sensor 10 and uses a shutter time of 400 ns.

Functions of this embodiment will be described hereunder.

The pulse laser beam 2 emitted from the pulse laser 1 is introduced into the optical fiber cable 3 by the lens 4. The optical fiber cable 3 is extended up to the vicinity of the unit 5 and the leakage oil therefrom is detected to introduce the pulse laser beam 2 into the irradiation head 7. The pulse laser beam 2 emitted from the irradiation head 7 uniformly irradiates the monitoring region 6 in pulsatory manner. Thus, the leakage oil 8 caused from the top of the unit 5 emits fluorescence as described above. The fluorescence is properly selected by the wavelength selection device 9 and then transmitted.

The camera controller 11 controls the shutter function of the fast-shutter-function-provided image sensor 10 in accordance with a signal sent from the synchronizing signal line 12 so that the shutter opens immediately after the pulse laser beam 2 disappears and moreover, so that the shutter closes after it is opened for a predetermined period.

As a result, an image signal is transmitted to the computer 13 through the camera controller 11 and an image processing is performed by the computer 13 and thereafter, it is decided whether leakage oil is present, and when decided, a signal is transmitted to the alarm 14, which outputs a warning to the neighborhood by means of light, sound, or synthetic voice.

As described above, because the detector of this embodiment makes the irradiation time and irradiation period of the pulse laser beam 2 different from the occurrence time and time width of the fluorescence emitted from the leakage oil 8, there is an advantage that it can be avoided to observe the pulse laser beam 2 as stray light.

Moreover, it is possible to avoid the phosphorescence or fluorescence emitted from a material present at the background of the leakage oil 8 by selecting the time. Furthermore, the fact that the wavelength of the pulse laser beam 2 is different from the transmission wavelength of the wavelength selection device 9 has an advantage that it can be avoided to observe the pulse laser beam 2 as stray light.

Furthermore, because operations of the fast-shutter-function-provided image sensor 10 are very fast and, hence, the influence of the disturbance light of a fluorescent lamp, sunlight, or incandescent lamp can be avoided, there is an advantage that the sensor can be used under indoor illumination or outdoor with much sunlight.

Figure 17A:
FIGS. 17A to 17C are views showing selectively detecting images of dummy leakage oil obtained by the oil detecting system of the first embodiment of the present invention.
Figure 17B:
Figure 17C:
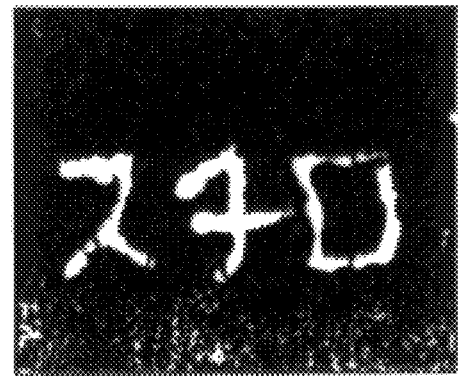
Figure 18A:
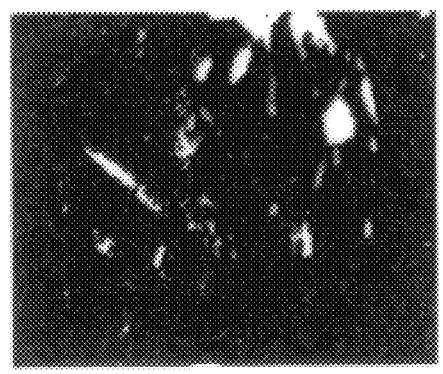
FIGS. 18A to 18C are views showing ordinary TV monitor images.
Figure 18B:
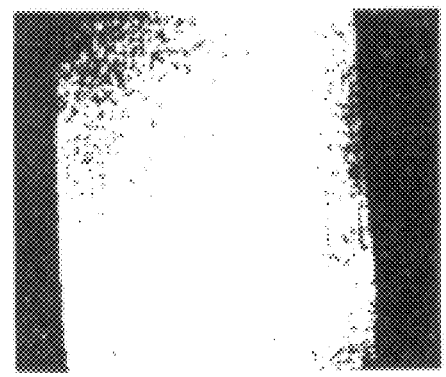
Figure 18C:
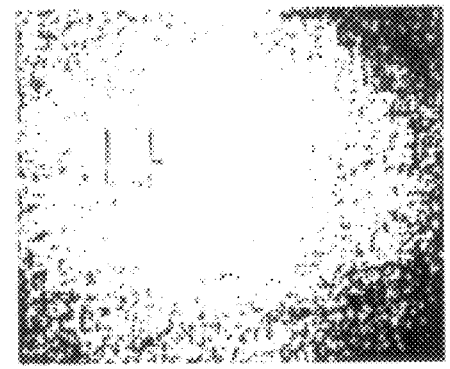

Images obtained by detecting a dummy leakage oil obtained by the detector of this embodiment under illumination of a fluorescent lamp are shown in FIGS. 17A to 17C and normal images are shown in FIGS. 18A to 18C.

FIGS. 17A and 18A show cases of using aluminum as a background material and coating it with steam turbine oil as a dummy leakage oil. Although selective detection of oil cannot be made by a normal TV monitor image, it is found that only the leakage oil can be selectively detected by the detector of this embodiment.

FIGS. 17B and 18B show cases of using Teflon (trade name) which is one of the fluorine-based resins as a background material and steam turbine oil as a dummy leakage oil. FIGS. 17C and 18C show cases of using an expanded resin as a background material and steam turbine oil as a leakage oil. According to the detector of this embodiment, only the leakage oil can be clearly and selectively detected in any case.

In general, by applying ultraviolet radiation to a fluorine-based resin, paint coated surface and expanded resin, a fluorescence is emitted. However, because the fluorescence wavelength and fluorescence emission period of these background materials are different from those of steam turbine oil, it is found that only the oil can be clearly separated. Therefore, a conventional leakage-oil detection system having no time resolving function cannot detect the oil dropped onto the above fluorescent materials. Moreover, it is very difficult to detect the oil at a bright place by the prior art.

Therefore, according to this first embodiment, by irradiating an oil to be detected with light having a wavelength suitable for the absorption wavelength of the oil, the leakage oil absorbs the light and emits fluorescence. The emission wavelength and emission period of the fluorescence are peculiar depending on the type or kind of the oils. Therefore, through the observation by the wavelength selection device 9 for observing the emission, i.e. fluorescence, wavelength of an oil and the fast-shutter-function-provided image sensor 10 for selectively observing only the period in which the oil emits light, it is possible to selectively observe only the feeble fluorescence of a leakage oil to be detected out of disturbances such as sunlight, illumination and light emitted from other material.

That is, according to this embodiment, it is possible to make the leakage oil 8 fluoresce by exciting it. By using the wavelength selection device 9 for selecting the fluorescence wavelength of the oil and performing the observation by the fast-shutter-function-provided image sensor 10 for selecting and observing only the period in which the oil emits fluorescence, it is possible to observe only the period in which only the fluorescence wavelength of the oil is emitted and selectively detect the feeble fluorescence of a purposed oil out of the disturbances such as light emitted from units and parts in a plant and illumination.

Moreover, according to this embodiment, high-sensitivity detection is realized because a pulse laser is used as the pulse-beam irradiation apparatus, a pulse laser beam has a small pulse width (nanoseconds to microseconds) and a preferable light monochromaticity and therefore, the pulse laser beam is easily separated from the fluorescence of an oil from the viewpoints of time and wavelength, and the pulse laser beam for making the oil fluoresce does not serve as the disturbance of the fast-shutter-function-provided image sensor 10.

Furthermore, according to this embodiment, it is possible to perform an observation suitable for the luminous wavelength for each type of the leakage oil to be detected without receiving the influence of disturbances due to illumination and other light-emitting substances. Furthermore, by comparing observation data values for a plurality of different wavelengths obtained by changing transmission wavelengths of a band-pass filter, it is possible to pattern an emission spectrum and distinguish between types of oils in accordance with the emission spectrum pattern.

Furthermore, according to this embodiment, it is possible to observe the feeble fluorescence of the leakage oil 8 as an image and detect the image of the leakage oil 8 by using the fast-shutter-function-provided image sensor 10 serving as a photodetector as an image intensifier having a fast-shutter function and an image intensifying function. Furthermore, by using a shutter function according to a fast gate, it is possible to select and observe only the period in which an oil fluoresces, set up a distinction with luminescence of a background material, and reduce disturbances.

Figure 19:
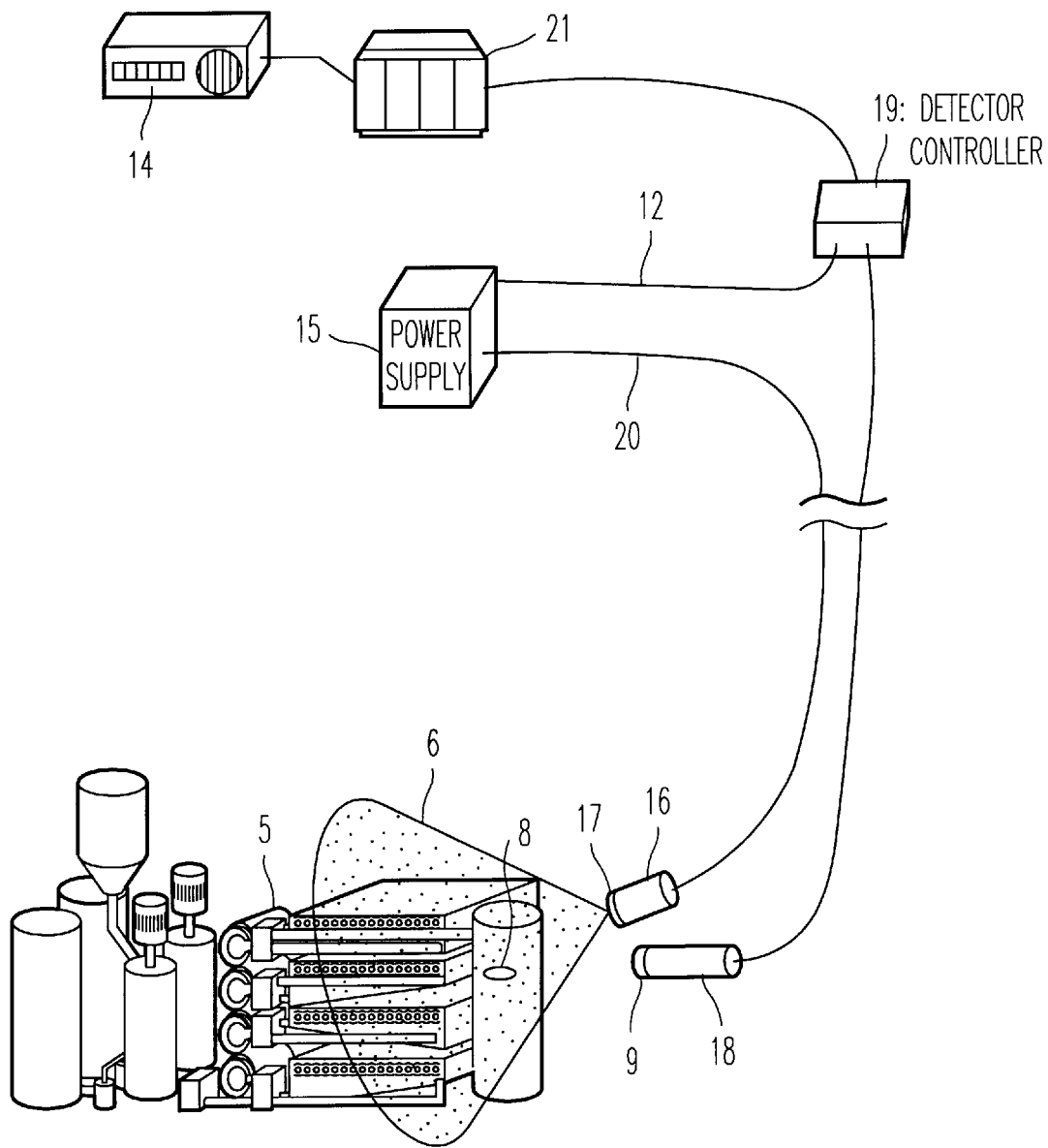
FIG. 19 is a view showing a structural arrangement of an oil detecting system according to a second embodiment of the present invention.

FIG. 19 is a block diagram showing the second embodiment of an oil detecting system of the present invention. With reference to FIG. 19, portions or parts the same as those of the first embodiment are provided with the same symbols or numerals for description. The oil detector of the second embodiment detects leakage oils of various types or kinds of units in a thermal power plant similarly to the first embodiment.

In the case of the first embodiment, the light irradiation apparatus comprises the pulse laser 1, lens 4, optical fiber cable 3 and irradiation head 7. In the case of the second embodiment, however, the light irradiation apparatus comprises a pulse-flash-lamp power supply 15, a flash lamp head 16 and an irradiation-side wavelength selection device 17 in order to reduce the cost of the light irradiation section and simplify the maintenance of the section.

Moreover, although the observation apparatus of the first embodiment comprises the wavelength selection device 9, fast-shutter-provided image sensor 10 and camera controller 11, the observation apparatus section of the second embodiment comprises the wavelength selection device 9, a normal photodetector 18 serving as a photodetector having a shutter function and a detector controller 19 in order to reduce the function so as to detect only the presence of a purposed leakage oil and simply the structure.

That is, as shown in FIG. 19, in the light irradiation apparatus, the pulse-flash-lamp power supply 15 and the flash lamp head 16 set nearby the monitoring region are connected each other by a transmission line 20. The flash lamp head 16 is provided with the irradiation-side wavelength selection device 17 for selecting only the fluorescence emitted from the leakage oil 8 caused in the monitoring region 6 by means of wavelength separation. Moreover, the photodetector 18 is able to select and detect only the period in which fluorescence is emitted from the leakage oil 8 or the luminous time width of the flash lamp head 16.

The pulse-flash-lamp power supply 15 is connected with the detector controller 19 by the synchronizing signal line 12 so that operations can be performed by synchronizing the luminous timing of the flash lamp head 16 with the observation by the photodetector 18.

The signal processing apparatus comprises a signal processor 21 for deciding a detection signal output from the detector controller 19 by a threshold value and the alarm 14 connected to the signal processor 21. In the case of the irradiation-side wavelength selection device 17, a most suitable device is selected in accordance with the absorption spectrum of the leakage oil 8.

A thermal power plant mainly uses the following five types of oils: steam turbine oil (S/T oil), gas turbine oil (G/T oil), mechanical hydraulic oil (MHC oil), electrical hydraulic oil (EHC oil) and mixed (mixture) oil obtained by mixing the above oils at optional rates. These oils have a rate of absorption in a range of a wavelength of approximately 190 to 360 nm as shown by the absorption-spectrum measurement data in FIGS. 2, 3, 4, 5 and 6 respectively. Therefore, the irradiation-side wavelength selection device 17 must have a performance of passing a wavelength region properly selected in a range of 190 to 360 nm.

Moreover, the luminous periods of leakage oils of steam turbine oil, gas turbine oil, mechanical hydraulic oil, electrical hydraulic oil and mixed oil are attenuated approximately as shown in FIGS. 7, 8, 9, 10 and 11. Therefore, to increase a signal-to-noise (S/N) ratio, it is more advantageous that the luminous time width of the flash lamp head 16 is short in order to avoid the influence of a disturbance.

As a flash lamp capable of achieving the above mentioned functions, it is possible to use a rare-gas pulse discharge lamp such as a xenon flash lamp or an excimer lamp such as a krypton-chloride discharge pulse lamp, krypton-fluoride pulse discharge lamp, xenon-chloride pulse discharge lamp, or xenon-fluoride pulse discharge lamp.

This embodiment uses a flash lamp head including an electric input of 15 J and a high-output pulse xenon lamp with a luminous pulse width of 7 ns as the flash lamp head 16.

Moreover, the irradiation-side wavelength selection device 17 uses a dielectric multilayer filter serving as a band-pass filter with a central wavelength of 260 nm and a band width of 40 nm. Furthermore, it is possible to use a colored glass filter or a filter using dispersion due to a grating as the irradiation-side wavelength selection device 17. Furthermore, it is preferable to use a device capable of selectively passing an emission spectrum from the leakage oil 8 as the wavelength selection device 9.

Luminous spectrums when applying light with a wavelength of 266 nm to five types of oils used for a thermal power plant are shown in FIGS. 12, 13, 14, 15 and 16. It is necessary to properly select a transmission wavelength of the wavelength selection device 9 in accordance with the luminous spectrum of each purposed oil and the disturbance light condition of a fluorescent lamp, sunlight, or incandescent lamp.

This second embodiment uses a dielectric multilayer filter serving as a band-pass filter whose transmission wavelength ranges between 290 and 350 nm as the wavelength selection device 9. Moreover, it is possible to use a colored glass filter or a filter using dispersion due to a grating as the wavelength selection device 9.

The photodetector 18 must have a sensitivity for a light wavelength transmitted through the wavelength selection device 9 and have a shutter function in a range from the approximate luminous period of the leakage oil 8 to the period in which the influence of disturbance light of a fluorescent lamp, sunlight, or incandescent lamp can be avoided, that is, in a range from approximately 100 ns to approximately 70 $\mu$s for five types of oils used for a thermal power plant.

As the above type of photodetector, it is possible to use a photomultiplier having a gate function, streak camera, avalanche photodiode provided with a fast-shutter function, photodiode or phototransistor. This embodiment uses a gate-function-provided photomultiplier at a gate time of 7 $\mu$s.

As a photodetector having the same function, it is possible to use an apparatus constituted by combining a photodetector such as a photomultiplier having no shutter function, photodiode, or phototransistor with a boxcar integrator to selectively capture the fluorescence emitted from the purposed leakage oil 8 by means of time resolving.

Functions of the second embodiment will be described hereunder.

A high pulse voltage is applied to the flash lamp head 16 from the pulse-flash-lamp power supply 15, and hence, the flash lamp head 16 emits light, selectively passes only a wavelength suitable for the absorption spectrum of an oil by the irradiation-side wavelength selection device 17, and uniformly irradiates the monitoring region 6 in pulsatory manner. As a result, the leakage oil 8 produced from the top of the unit 5 emits fluorescence as described above. The fluorescence is properly selected and transmitted by the wavelength selection device 9.

The detector controller 19 operates the gate function of the photodetector 18 by synchronizing the function with light emission of the flash lamp head 16 in accordance with a signal sent from the synchronizing signal line 12. As a result, it is possible to detect only the fluorescence emitted from the leakage oil 8 by time-resolving it. The detection signal is transmitted to the signal processor 12 through the detector controller 19 and a signal for operating the alarm 14 is transmitted when the signal exceeds a certain threshold value. Thus, the alarm 14 outputs warning to the neighborhood by light, sound or synthetic voice.

As described above, the detector of this second embodiment is able to easily detect the presence or absence of a purposed leakage oil by using a function obtained by simplifying the first embodiment and thus, it has the same function as that of the first embodiment except that the leakage oil cannot be captured as a two-dimensional image.

Therefore, the second embodiment is able to emit light containing the absorption wavelength of an oil to be detected by a flash lamp because of using a flash lamp as the pulse-beam irradiation apparatus and serve as an irradiation apparatus superior in maintainability.

Moreover, this embodiment is able to select a wavelength containing the absorption wavelength of an oil out of the wavelengths emitted by a flash lamp, to emit it because of using a band-pass filter as the irradiation-side wavelength selection device 17, to make the oil effectively emit light and to moreover prevent the light having a wavelength serving as a disturbance for observation from passing.

Furthermore, by changing the transmission wavelengths of the band-pass filter, it is possible to obtain an any irradiation wavelength. Furthermore, by comparing luminescence observation data values for a plurality of irradiation wavelengths each other, it is possible to pattern the shape of an excitation spectrum and distinguish between types of oils in accordance with the excitation spectrum pattern.

Furthermore, this embodiment makes it possible to observe the feeble fluorescence of the leakage oil 8 as a signal and detect the presence or absence of the leakage oil 8 by constituting the photodetector 18 as a photomultiplier combined with either of a fast-gate-function-provided photomultiplier and a boxcar integrator. Thus, it is possible to observe the feeble fluorescence of the leakage oil 8 as a signal and detect the presence or absence of the leakage oil 8. Moreover, by using the fast gate and the shutter function of the boxcar integrator, it is possible to select only the period in which an oil fluoresces and observe the fluorescence, set up a distinction with luminescence of a background material, and reduce disturbances.

Still furthermore, the present invention provides the following third to eighth embodiments of the oil detecting systems for detecting the oil leakage through the detection or observation of the leakage oil film thickness, leakage oil area and leakage oil quantity as well as the detection of the leakage oil.

The third embodiment of the present invention is an oil detecting system particularly adapted to detect leakage oil from units or parts in a thermal power plant.

Figure 20:
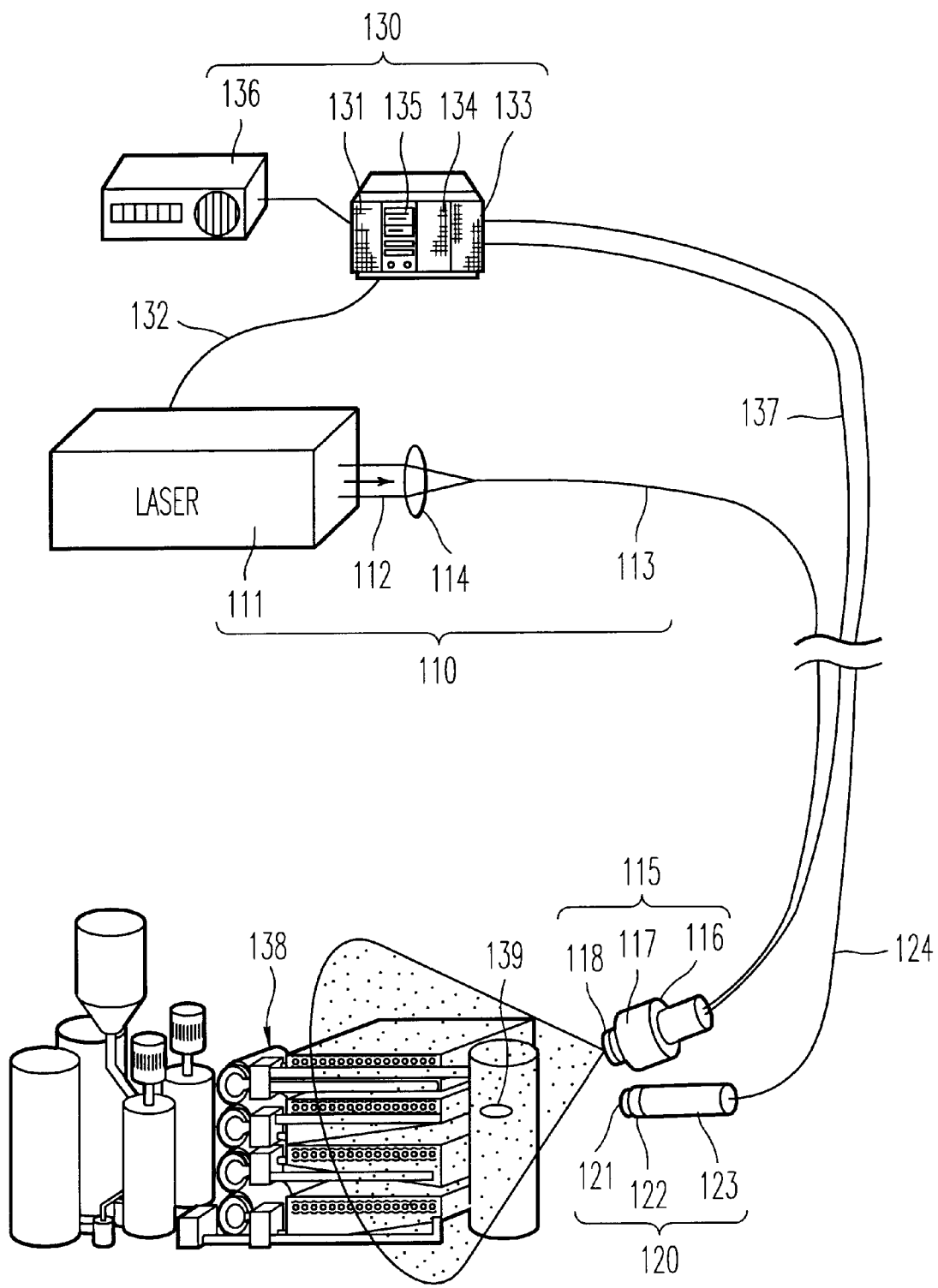
FIG. 20 is a view showing a structural arrangement of an oil detecting system according to a third embodiment of the present invention.

An oil detecting system of FIG. 20 generally comprises an irradiation apparatus 110, an observation apparatus 120 and a processing apparatus 130.

The irradiation apparatus 110 comprises a pulse beam source 112 such as Xe flash lamp, a lens 114 for introducing an irradiated pulse beam 112, a throttle optical fiber 113 for transmitting the introduced pulse beam 112 up to the vicinity of a monitoring region and an irradiation head 115 for irradiating a purposed monitoring region with the transmitted pulse beam 112. The irradiation head 115 includes an irradiation wavelength selection apparatus 116 provided with a plurality of wavelength selection devices to select irradiation wavelengths of the pulse beam 112, a light-source deterioration correction apparatus 117 for correcting the measurement accuracy of a film thickness by measuring the irradiation intensity of the pulse beam 112 and a lens 118 for applying the pulse beam 112 by enlarging it up to a size suitable for a monitoring region.

The observation apparatus 120 comprises an observation filter 121 serving as a wavelength selection device for selecting and observing the luminescence wavelength of a leakage oil, a lens 122 for adjusting a region to be observed to the monitoring region, and a photomultiplier 123 having a gate function as an light detection element for observing the luminescence of the oil.

The processing apparatus or processor 130 comprises a timing controller 131 for controlling the irradiation timing of the pulse beam source 111, a timing signal transmission line 132 for transmitting a timing signal output from the timing controller 131 to the pulse beam source 115, a signal integration apparatus 133 for integrating output signals of the photomultiplier 123, a film-thickness computing apparatus 134 for computing the film thickness of leakage oil, an output monitor 135 for displaying the processing result of the signal integration apparatus 118 and the film thickness obtained by the film-thickness computing apparatus 134, and an alarm 136 for communicating the presence or absence of oil leakage to persons.

The oil leaking from a unit is hereafter referred to as a leakage oil 139. The leakage oil 139 is an oil used for a thermal power plant as an example. Oils used for a thermal power plant include gas turbine oil (G/T oil), steam turbine oil (S/T oil), and electrical hydraulic oil (EHC oil) as high-pressure hydraulic oil. It is assumed that the leakage oil 139 to be detected hereafter is the gas turbine oil leaking from a unit 138 set under a normal illumination condition by a fluorescent lamp or the like. Moreover, the leakage oil 139 contains a leakage oil with dust attached to the surface, a leakage oil changed in quality like lard after leakage, a leakage oil of semi-solid lubricant such as grease, and a leakage oil of solid lubricant.

Functions and advantages of this third embodiment will be described hereunder.

It is more preferable that the pulse beam source 111 has a short pulse width of luminescence and a high output. This is because when the pulse width of luminescence is short, longer period in which an oil luminesces after irradiation of the pulse beam 112 can be selected and observed and the S/N ratio hence increases. Moreover, when the source 111 has a high output, it is possible to expand a monitoring region. Hereafter, a case is described in which the pulse beam source 111 uses a Xe flash lamp.

The pulse beam source 111 is made luminous by the timing controller 131. The repetition cycle of the luminescence is set to 3 Hz because it can be optionally determined in accordance with a time interval to be monitored. The pulse beam 112 emitted from the pulse beam source 111 is throttled by the lens 114 and enters the optical fiber 113. Then, the pulse beam 112 is led to the irradiation head 115 through the optical fiber 113. The optical fiber 113 is made of an optical fiber with a quartz core because it is enough that the optical fiber 113 can transmit the pulse beam 112. The optical fiber 113 makes it possible to easily lead the pulse beam 112 to the irradiation head 115 set at a remote and narrow portion.

The irradiation head 115 selects the irradiation wavelengths of the pulse beam 112 by the irradiation wavelength selection apparatus 116 provided with a plurality of wavelength selection devices and capable of selecting the irradiation wavelengths of the pulse beam 112. The wavelength selection device of the irradiation wavelength selection apparatus 116 uses a colored-glass filter or interference filter having a general flat shape. It is necessary that the irradiation wavelength includes the absorption wavelength of the leakage oil 139 of the gas turbine oil and has a wavelength capable of computing a film thickness in accordance with the fluorescence intensity of the oil 139 when the oil is excited and made to luminesce.

The excited light absorbed by an oil with a film thickness d and the fluorescence emitted from the oil have the relation shown in the following expression (1).

[Expression 1]

$$I_f = \frac{I_a \cdot \alpha}{\beta}(1 - e^{-\beta d}) \qquad (1)$$

Figure 21:
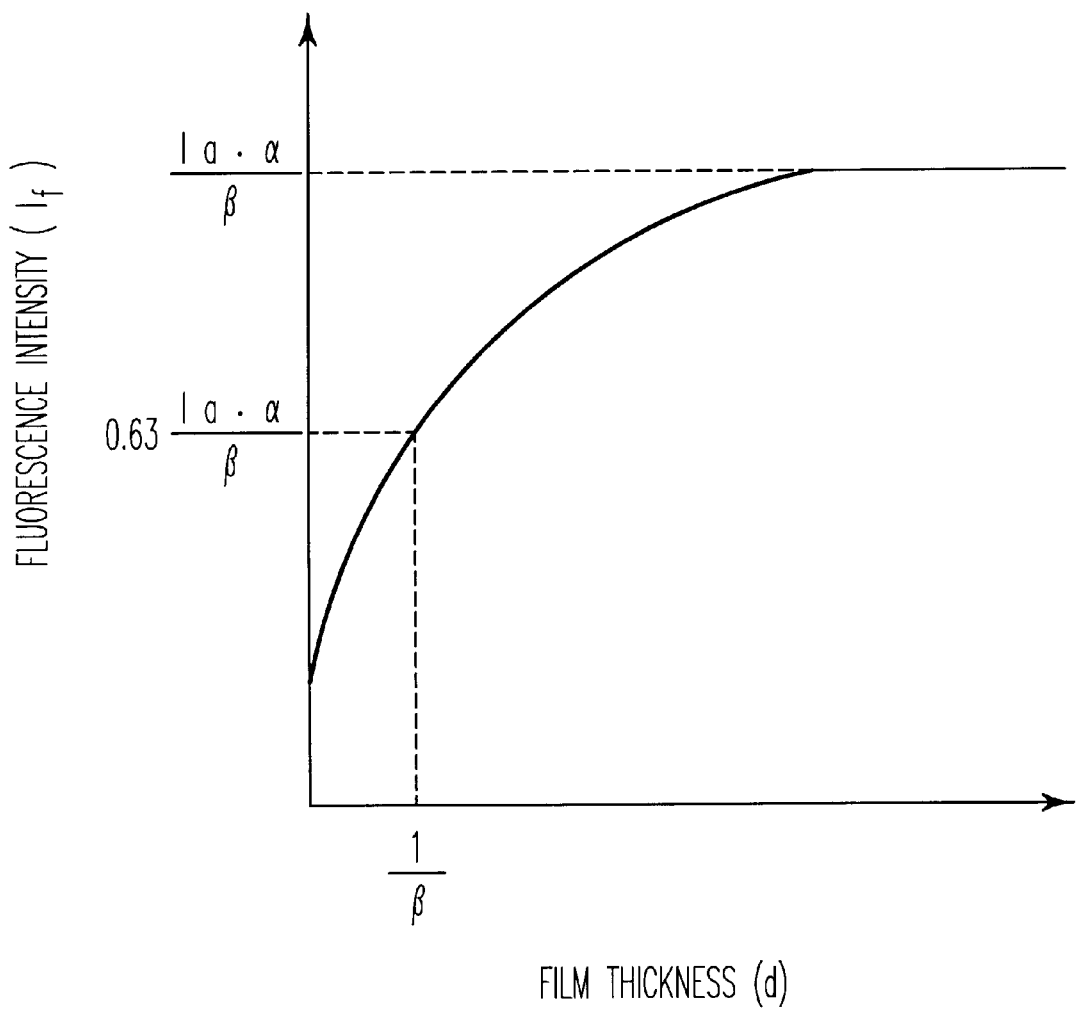
FIG. 21 is a graph showing a relationship between a film thickness and a fluorescence intensity of an oil.

$I_a$: Excited-light intensity, $I_f$: Fluorescence intensity, $\alpha$: Fluorescence efficiency, $\beta$: Absorption coefficient FIG. 21 shows the expression (1) by graphing it. With reference to FIG. 21, when a film thickness is small, the film thickness d corresponds to the fluorescence intensity $I_f$ one to one and, therefore, the film thickness d can be computed in accordance with the fluorescence intensity $I_f$. However, when the film thickness d increases, the film thickness cannot be computed because the fluorescence intensity $I_f$ is saturated. In this case, the saturation of the fluorescence intensity greatly depends on the absorption coefficient of the term $e^{-\beta d}$ in the expression (1). Therefore, to measure a purposed film thickness, it is necessary to select an irradiation wavelength in which a fluorescence intensity is not saturated in a measurement range and a film thickness d corresponds to the fluorescence intensity $I_f$ one to one.

Thus, it is necessary to determine a proper absorption coefficient β and to select an irradiation wavelength meeting this absorption coefficient in accordance with the absorption characteristic of an oil to be detected. First, in the case of the film thickness computing apparatus 134, when the fluorescence intensity $I_f$ in the expression (1) is $I_a \cdot \alpha\,(1-e^{-1})/\beta$ or less, a film thickness d is set so that the film thickness d corresponds to a fluorescence intensity $I_f$ one to one and it can be computed in accordance with the fluorescence intensity. Therefore, it is necessary that a value β d in the term of $e^{-\beta d}$ meets the following expression (2).

[Expression 2]

$$d \cdot \beta \leq 1 \qquad (2)$$

Moreover, when setting a purposed range to $0$–$10^{-4}$ m (100 μm), the value β must meet the following expression (3).

[Expression 3]

$$\beta \leq 10^4 \text{ m}^{-1} \qquad (3)$$

Figure 3:
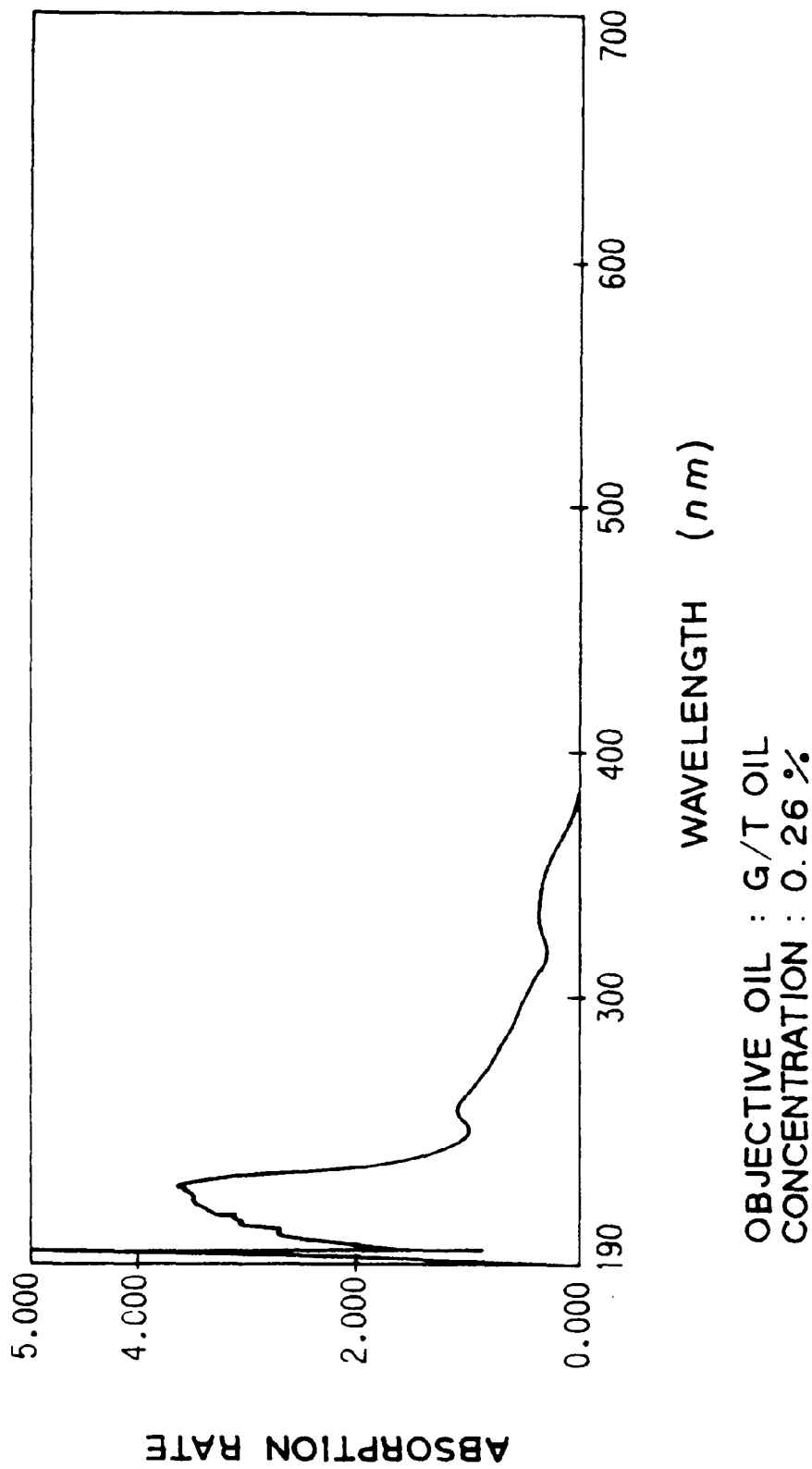
FIG. 3 is a graph showing an absorption-spectrum measurement data of a gas turbine oil as an oil to be detected.
Figure 4:
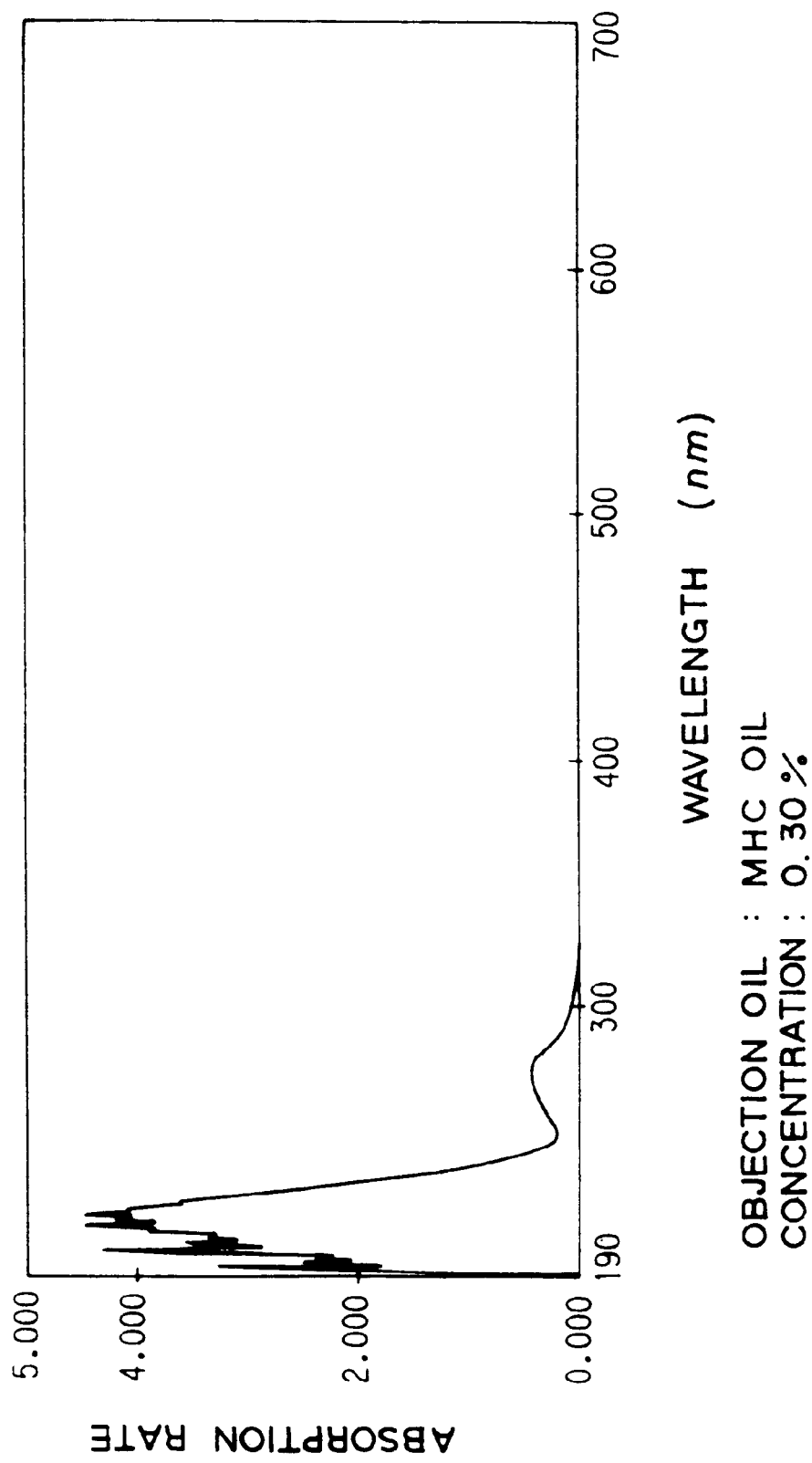
FIG. 4 is a graph showing an absorption-spectrum measurement data of a mechanical hydraulic oil as an oil to be detected.

FIG. 3 shows the absorption wavelength of gas turbine oil measured by a spectrophotometer. The absorbance A has the relation shown by the following expression (4).

[Expression 4]

$$A = \beta c L \qquad (4)$$

c: Concentration of oil, L: Optical path length

With reference to FIG. 3, the oil concentration c equals 0.0026, and the optical path length L equals 0.01 m. Therefore, by substituting these values and the value of the expression (3) for the expression (4), the absorbance A is equal to or less than 0.26. In this case, by assuming the absorbance A as 0.26 and selecting a wavelength having the value 0.26 in accordance with the absorption characteristic shown in FIG. 3, it can be concluded that an irradiation wavelength of approximately 360 nm is preferable. Therefore, to measure the gas turbine oil with a film thickness of 0 to 10 μm, a wavelength selection device in which an irradiation wavelength comes to 360 nm is provided for the irradiation wavelength selection device 116. Moreover, the film thickness computing conditions of the excited-light intensity $I_a$, fluorescence efficiency α and absorption coefficient β in the above case are stored in the film thickness computing apparatus 134 so that the film thickness d can be obtained from the expression (1) and the fluorescence-intensity measured value.

The following Table 1 shows irradiation wavelengths obtained to measure a film thickness of 0 to 100 μm for various types of oils.

TABLE 1

Irradiation Wavelength used for Measurement of Oil Film Thickness 100 μm

| Type of Oil | Irradiation Wavelength (nm) |
| --- | --- |
| Gas turbine oil | 360 |
| Steam turbine oil | 280 |
| High-pressure hydraulic oil | 280 |

Figure 2:
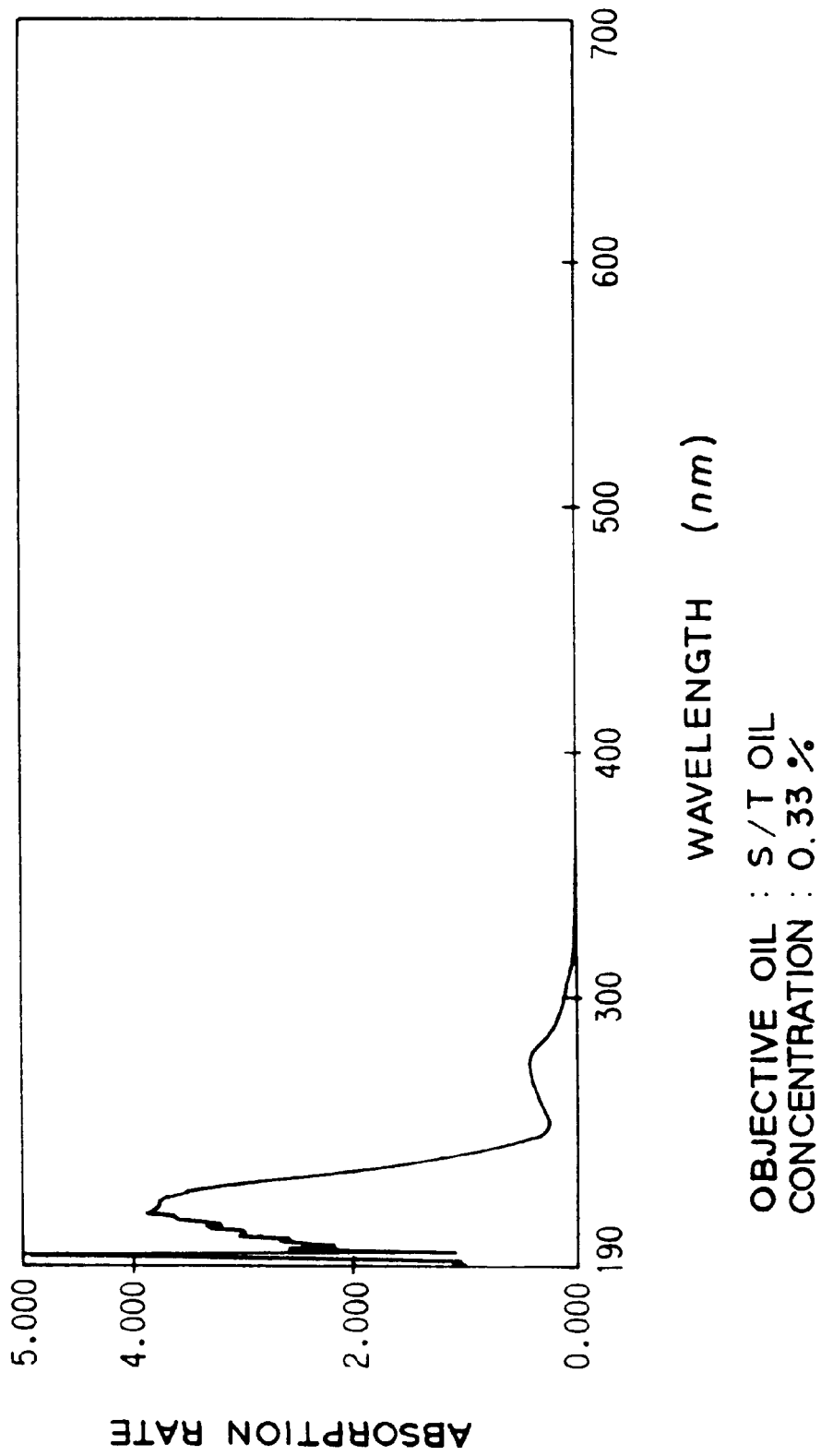
FIG. 2 is a graph showing an absorption-spectrum measurement data of a steam turbine oil as an oil to be detected.
Figure 5:
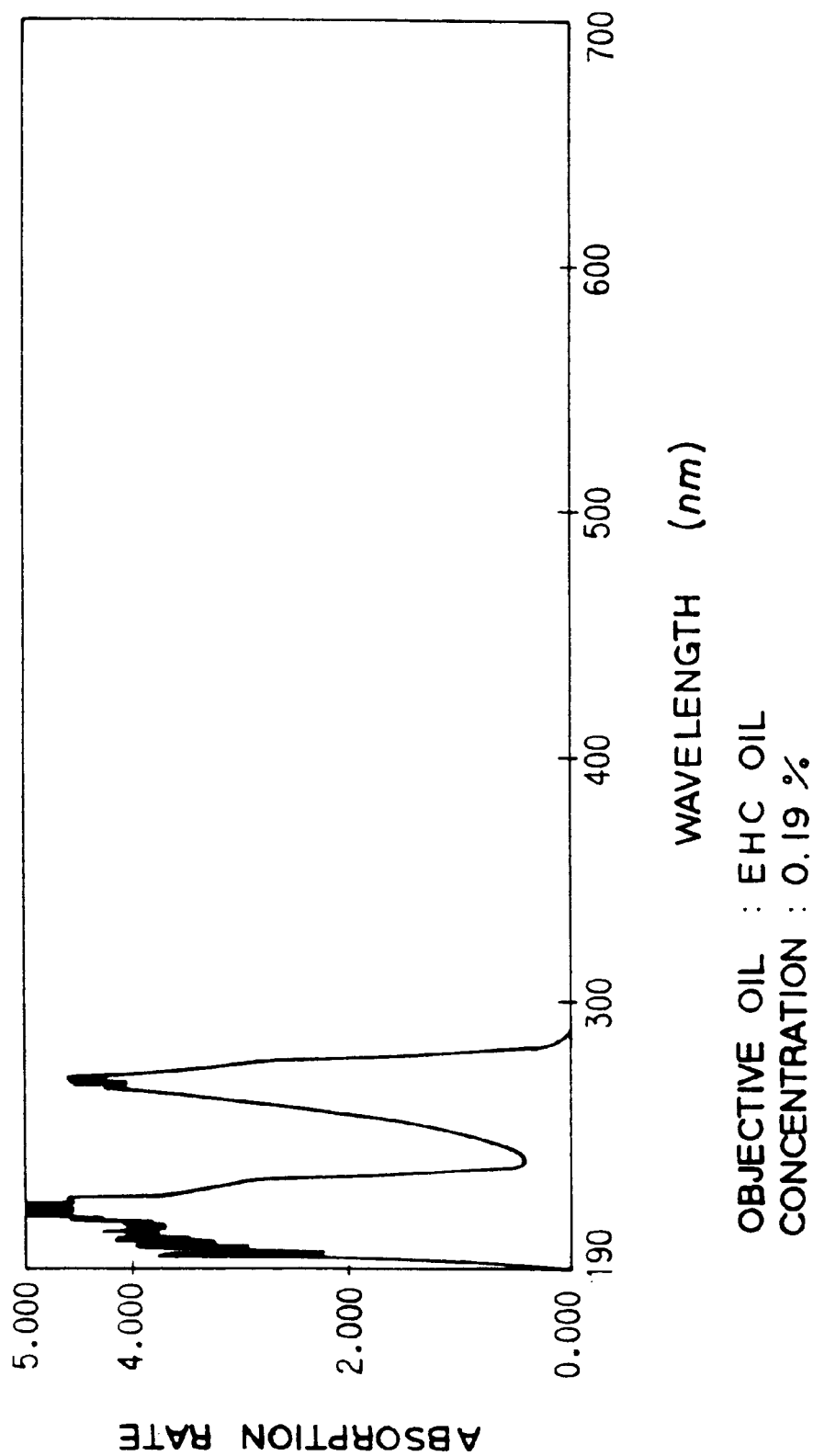
FIG. 5 is a graph showing an absorption-spectrum measurement data of an electrical hydraulic oil as an oil to be detected.
Figure 6:
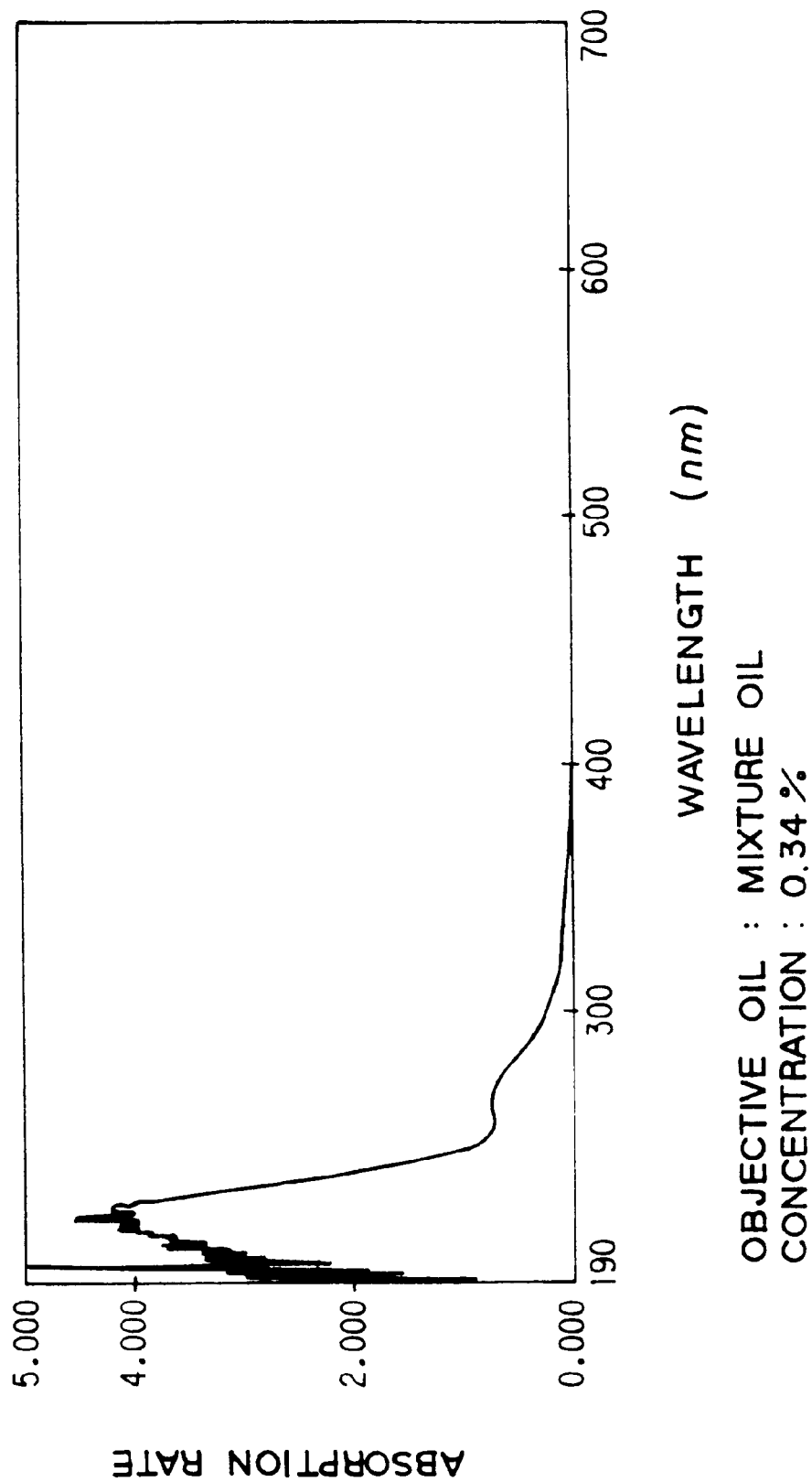
FIG. 6 is a graph showing an absorption-spectrum measurement data of a mixture oil as an oil to be detected.

Moreover, as mentioned with reference to the first embodiment, FIG. 2 shows the absorption wavelength of steam turbine oil and FIG. 5 shows the absorption wavelength of an electrical hydraulic oil. In accordance with Table 1, wavelength selection devices allowing an irradiation wavelength to be set to 280 and 360 nm are provided for the irradiation wavelength selection apparatus 116. Furthermore, film thickness computing conditions of various oils are stored in the film thickness computing apparatus 134 so that a film thickness can be obtained from the film thickness conditions and the expression (1).

Thus, the pulse beam 112 with an irradiation wavelength of 360 nm is applied from the irradiation head 115 to the leakage oil 139 by the irradiation wavelength selection apparatus 116. The leakage oil 139 absorbs the pulse beam 112 and emits fluorescence. The fluorescence has the fluorescence wavelength shown in FIG. 13 because the leakage oil 139 is gas turbine oil. In a monitoring region, there are disturbance light such as sunlight and a fluorescent lamp and luminescence of background units 138 in addition to the fluorescence of the leakage oil 139.

Figure 12:
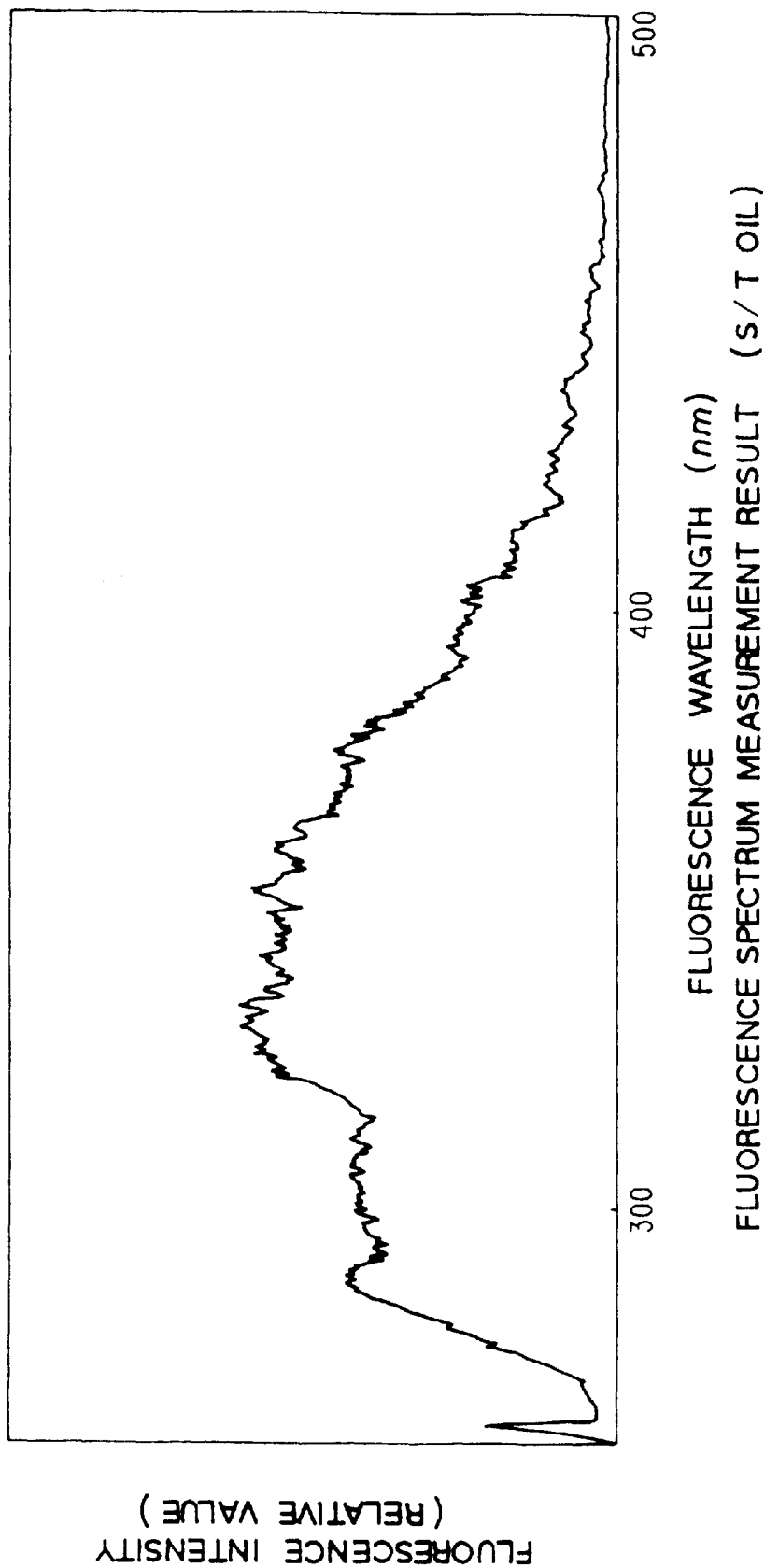
FIG. 12 is a graph showing an emission spectrum measurement data of a steam turbine oil to be detected.
Figure 13:
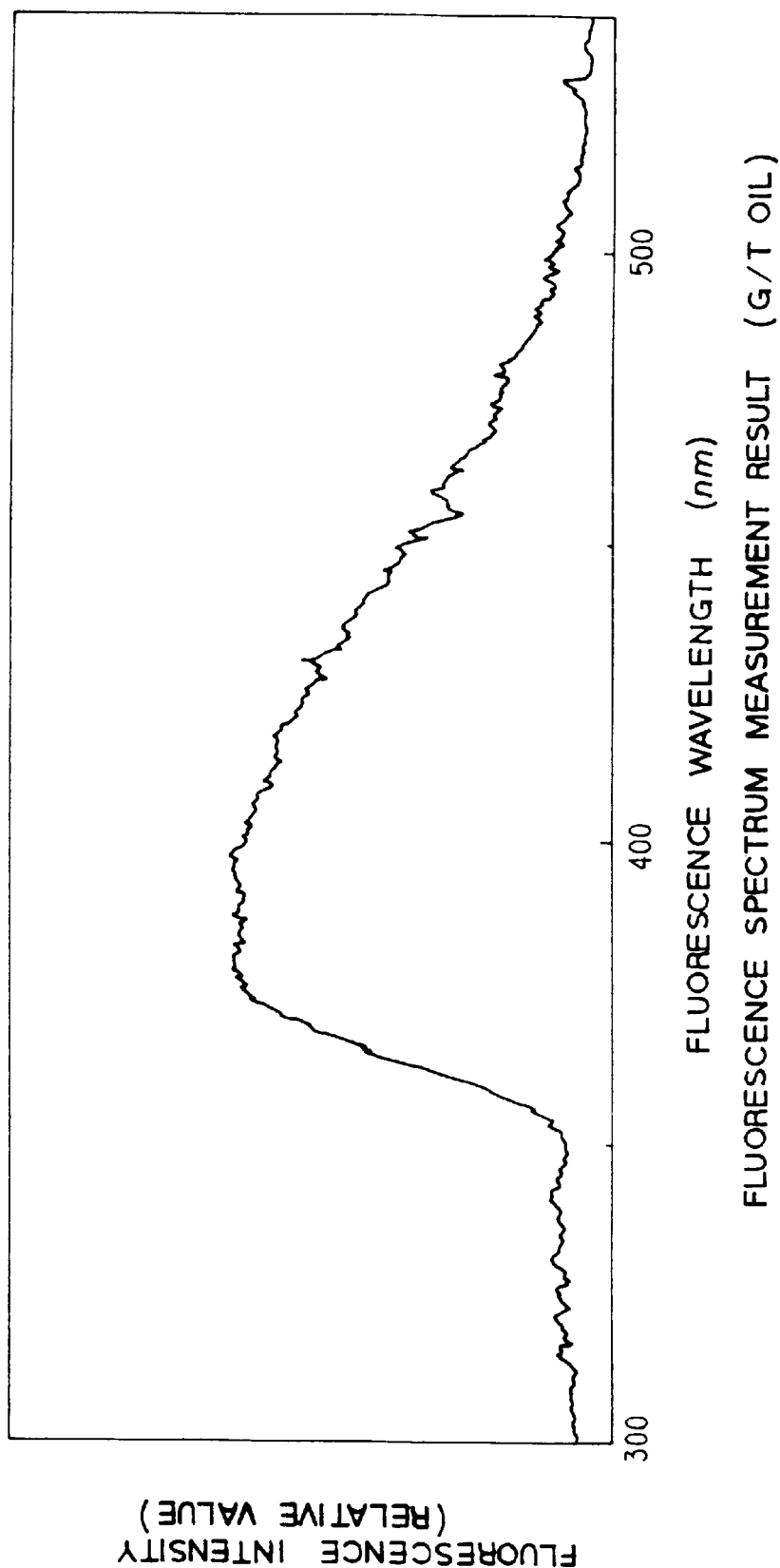
FIG. 13 is a graph showing an emission spectrum measurement data of a gas turbine oil as an oil to be detected.
Figure 14:
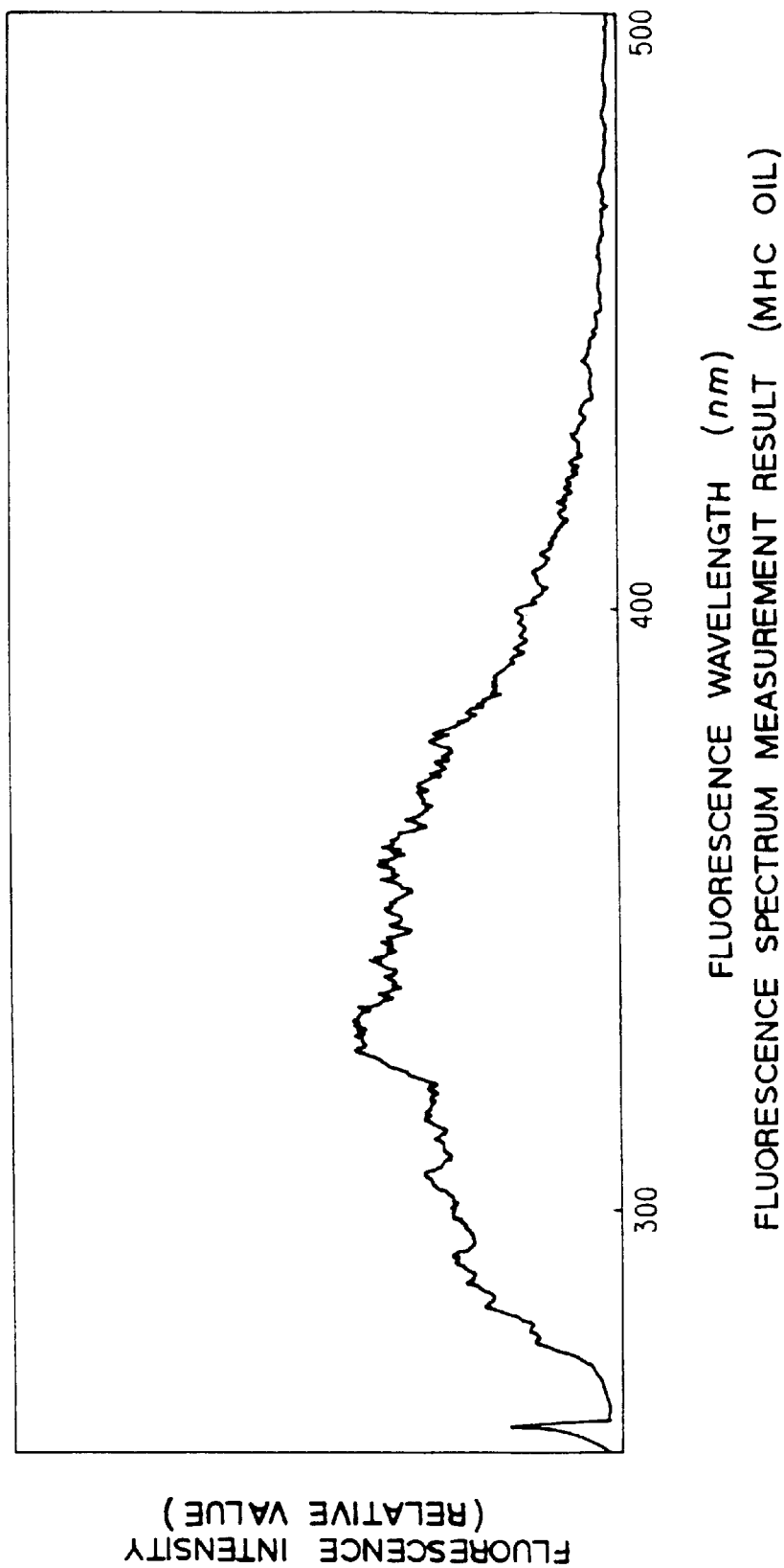
FIG. 14 is a graph showing an emission spectrum measurement data of a mechanical hydraulic oil as an oil to be detected.
Figure 15:
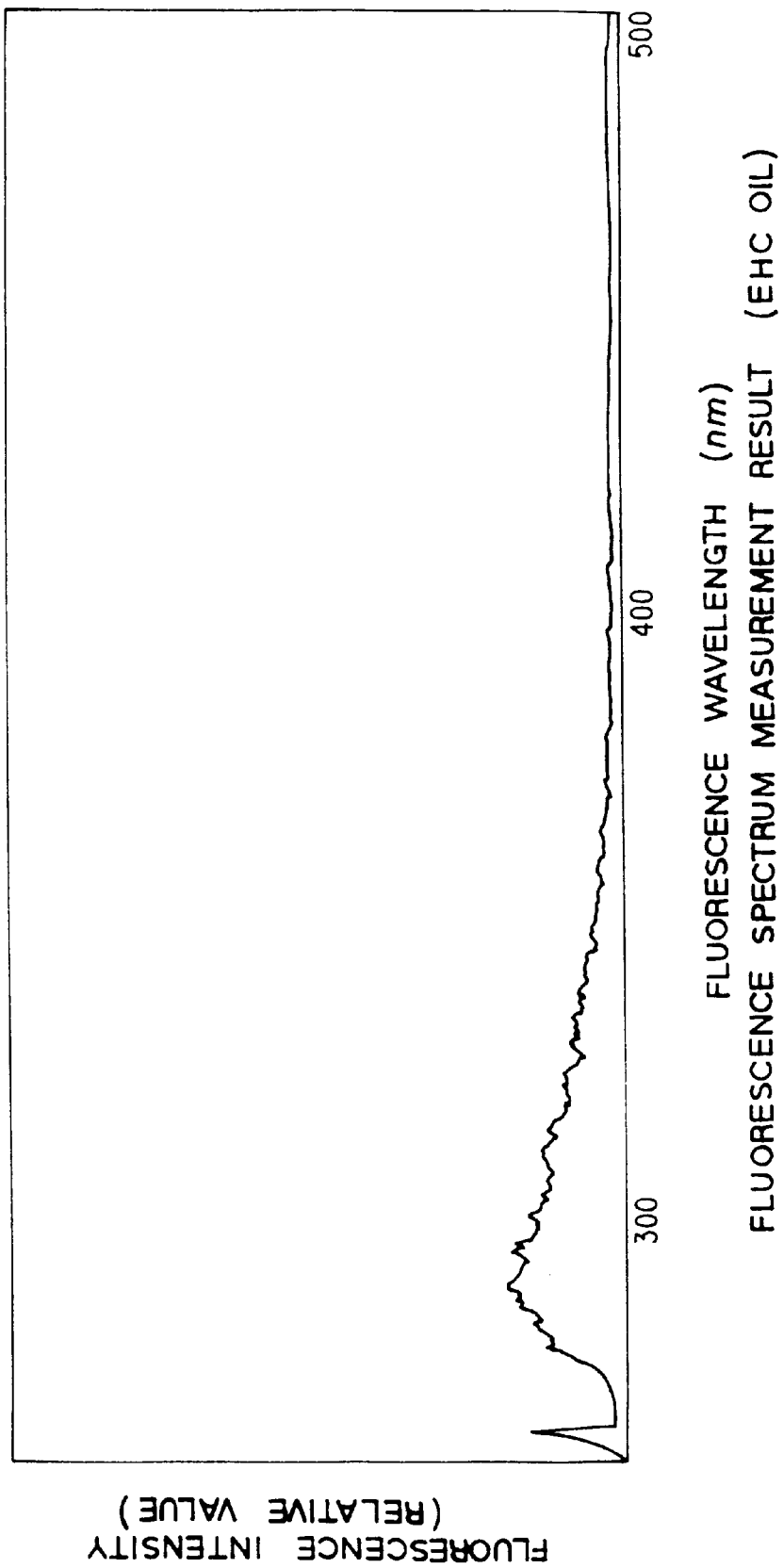
FIG. 15 is a graph showing an emission spectrum measurement data of an electrical hydraulic oil as an oil to be detected.
Figure 16:
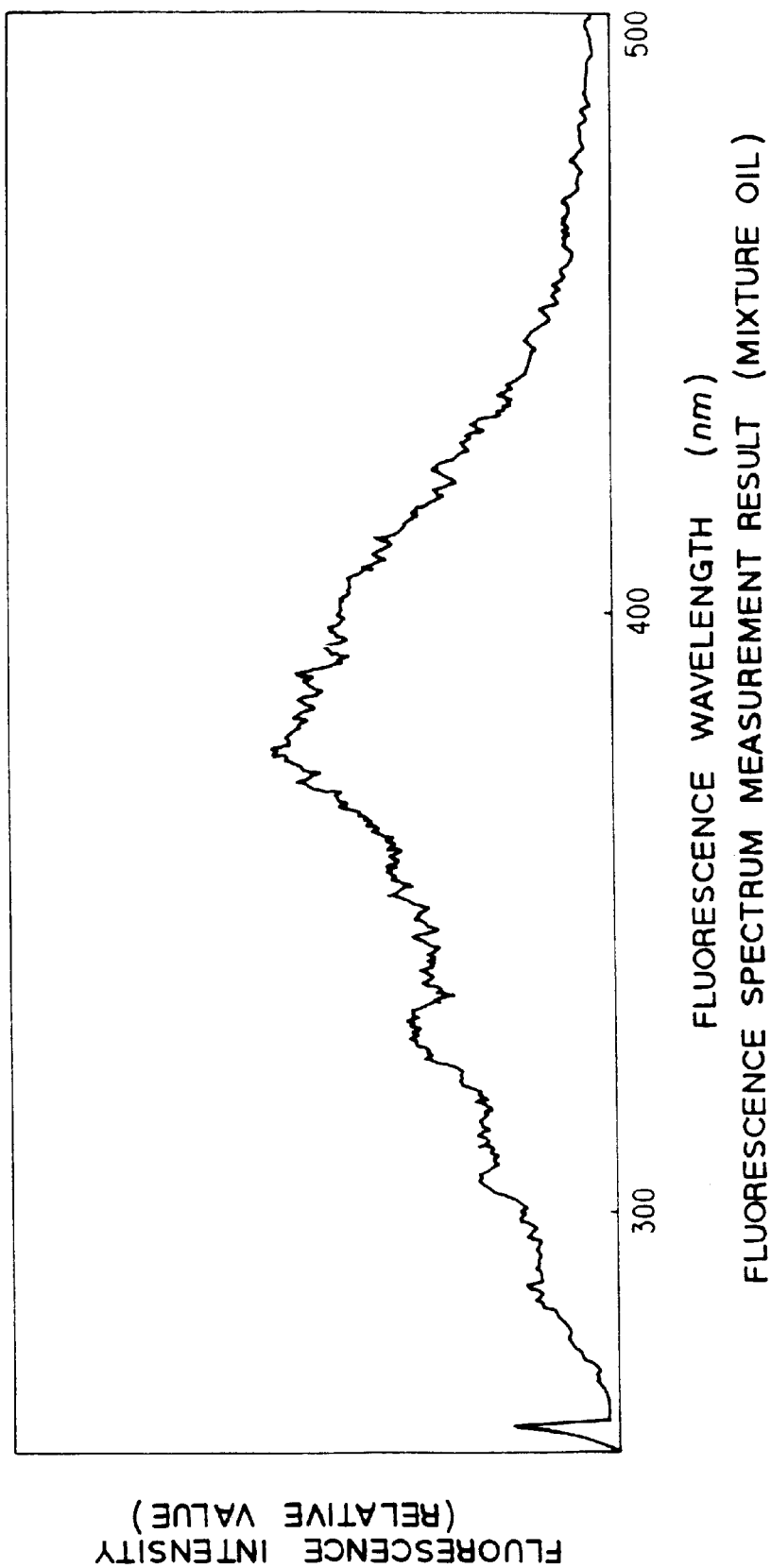
FIG. 16 is a graph showing an emission spectrum measurement data of a mixture oil as an oil to be detected.

Therefore, the fluorescence of the leakage oil 139 is observed by the photomultiplier 123 of the observation apparatus 120 in which the observation wavelength of the observation filter 121 is set to 400–450 nm. The observation filter 121 of the observation apparatus 120 is selected so that the luminescence wavelength of gas turbine oil can be selected and observed. Moreover, it is considered that the irradiation wavelength 360 nm for making the leakage oil 139 fluoresce is not overlapped with an observation wavelength to be selected by the observation filter 121. FIGS. 15 and 12 show luminescence wavelengths of other types of oils for reference as mentioned hereinbefore. By selecting the observation wavelength of the observation filter 121 for each type of oil, it is possible to selectively detect only a specified type of the leakage oil.

Figure 7:
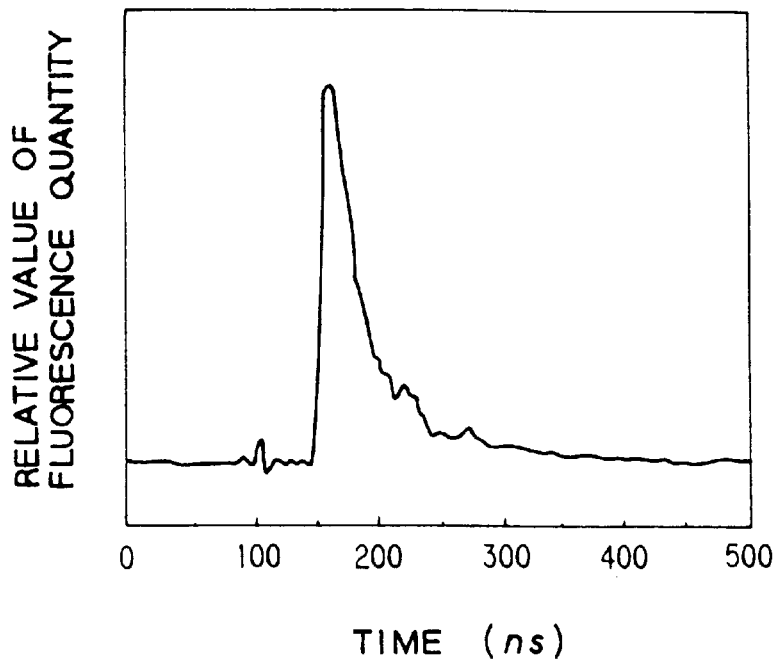
FIG. 7 is a graph showing a luminous period date of a steam turbine oil as an oil to be detected.
Figure 8:
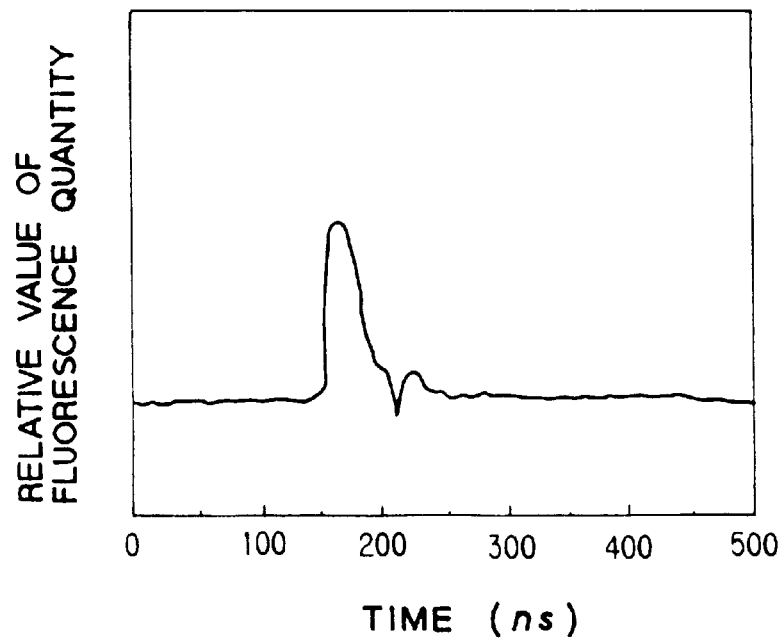
FIG. 8 is a graph showing a luminous period date of a gas turbine oil as an oil to be detected.
Figure 9:
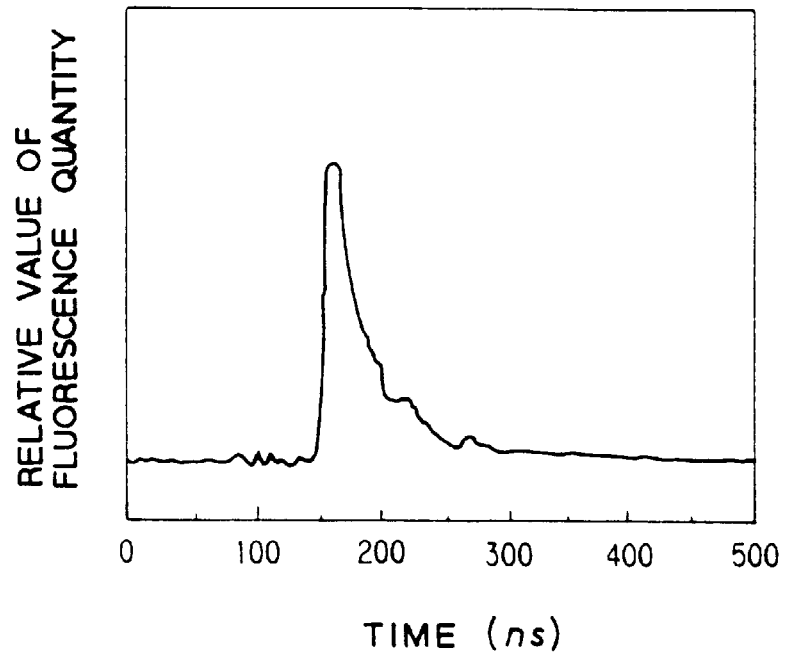
FIG. 9 is a graph showing a luminous period date of a mechanical hydraulic oil as an oil to be detected.
Figure 10:
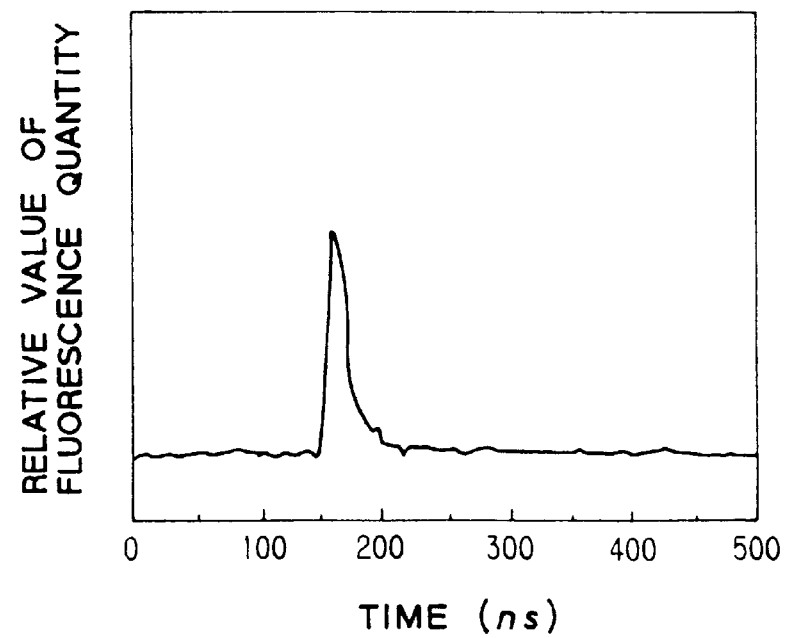
FIG. 10 is a graph showing a luminous period date of an electrical hydraulic oil as an oil to be detected.
Figure 11:
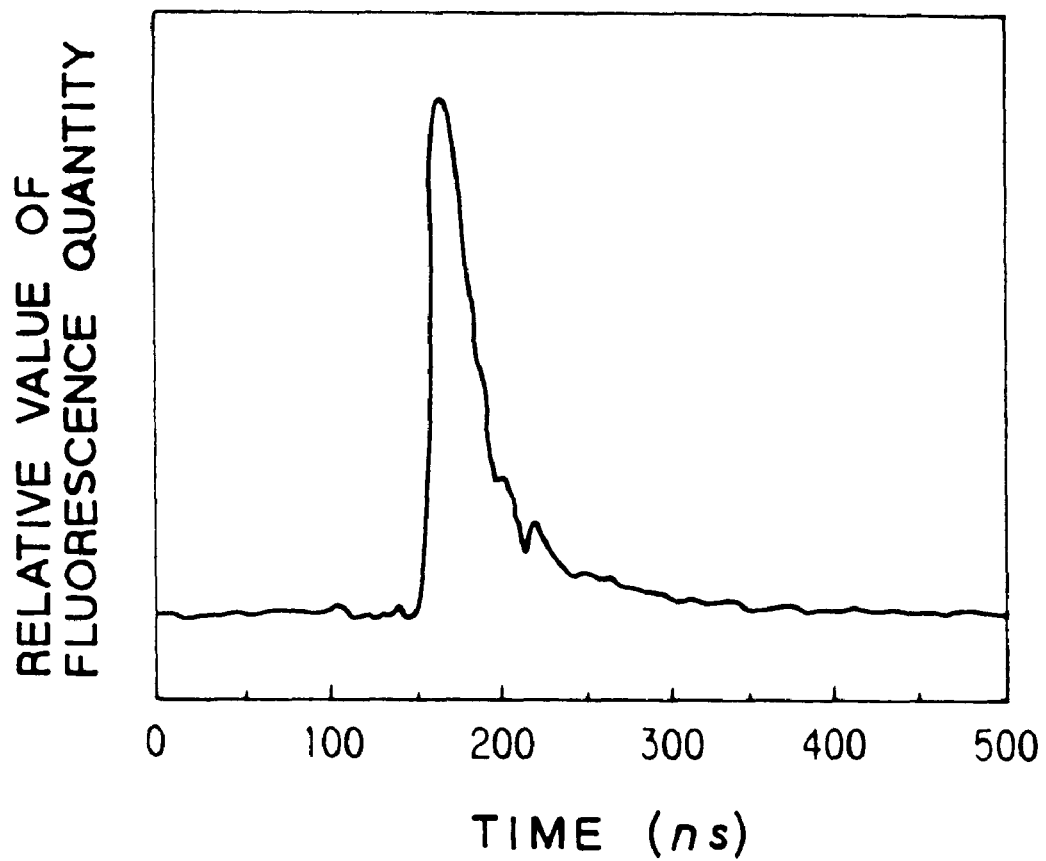
FIG. 11 is a graph showing a luminous period date of a mixture oil as an oil to be detected.

The luminescence times of the leakage oil such as steam turbine oil, gas turbine oil and electrical hydraulic oil as high-pressure oil are represented by FIGS. 7, 8 and 10, respectively as mentioned before from which it is observed that the times are attenuated within approximately 500 ns. For this reason, in order to increase the S/N ratio, it is advantageous for the pulse beam 112 to have a time width sufficiently longer than the luminescence time of the oil.

A detection signal detecting the fluorescence of the leakage oil 139 observed by the photomultiplier 123 of the observation apparatus 120 is transmitted to the processing apparatus 130. The processing apparatus 130 extracts only signals while the leakage oil 139 fluoresces after irradiation of the pulse beam 112 in accordance with the irradiation timing of the timing controller 131. Each signal is a leakage-oil detection signal detecting the fluorescence of the leakage oil 139. By sending the leakage-oil detection signal to the film thickness computing apparatus 134, it is possible to obtain a film thickness from the film thickness computing conditions previously stored by the film thickness computing apparatus 134 and the expression (1).

As the result of the above functions, it is possible to detect the fluorescence of the leakage oil 139 at a high sensitivity even by the observation-wavelength selection function of the observation filter 121 of the observation apparatus 120 and the observation-time selection function of the processor apparatus 130 even if disturbance light such as sunlight or a fluorescent lamp or the fluorescence of background units is present.

Moreover, by selecting an irradiation wavelength by the irradiation wavelength selection apparatus 116 and making the leakage oil 139 fluoresce, it is possible to adjust a measurable film-thickness range and obtain the film thickness of the leakage oil 139 by the film thickness computing apparatus 134 recording the film thickness computing conditions and the expression (1) even if disturbance light such as sunlight or a fluorescent lamp or luminescence of background units is present. The oil in the above case can use gas turbine oil, steam turbine oil or electrical hydraulic oil.

Furthermore, it is possible to decide the presence or absence of the oil leakage in accordance with the film thickness and display the presence or absence of the oil leakage, film thickness, or leakage oil detection signal on the output monitor 135 according to necessity. Furthermore, it is possible to communicate oil leakage to persons through a warning lamp or sounds by the alarm 136.

The function and effect of the light-source deterioration correction apparatus 117 according to the present embodiment will be described hereunder.

When the irradiation intensity $I_a$ of the pulse beam source 111 is degraded due to the aged deterioration, the fluorescence intensity $I_f$ deteriorates even for the same film thickness in accordance with the expression (1). In this case, the processing apparatus 130 cannot detect that the irradiation intensity deteriorates but it decides that the fluorescence intensity $I_f$ is deteriorated due to the decreasing of the film thickness of the leakage oil 139. Therefore, the film-thickness measurement accuracy is degraded due to the deterioration of the pulse beam source 111.

Therefore, the deterioration of the measurement accuracy is improved by means of the light-source deterioration correction apparatus 117 provided for the irradiation head 115. The irradiation intensity $I_m$ of the pulse beam 112 emitted from the irradiation head 115 is measured by the light-source deterioration correction apparatus 117. Then, a deterioration rate is obtained by using the previously stored reference-irradiation-intensity $I_b$ in accordance with the following expression (5).

[Expression 5]

$$\gamma = \frac{I_b}{I_m} \quad (5)$$

A signal representing the deterioration rate is sent to the processing apparatus 130 through a signal transmission line 137 and the deterioration rate is then multiplied by the detection signal of the photomultiplier 123. When considering the above operation in accordance with the expression (1), it is concluded that the fluorescence intensity at the reference irradiation intensity $I_b$ is computed from the case of the deteriorated irradiation intensity $I_m$. A film thickness is obtained from the previously stored film thickness computing conditions and the expression (1) by calculating the deterioration rate γ for the detection signal of the photomultiplier 123 and extracting a leakage oil detection signal from a correction detection signal in which the deterioration of the irradiation intensity of the pulse beam source 111 is corrected.

As the result of the above functions, it is possible to correct the deterioration of the irradiation intensity of the pulse beam source 111 caused by the aged deterioration and prevent the film thickness measurement accuracy from deteriorating by obtaining the film thickness of the leakage oil 139 from a correction detection signal obtained by computing the deterioration rate γ for the detection signal of the photomultiplier 123.

Then, the functions and effects of the signal integration processing apparatus 133 according to the present invention will be described hereunder.

The deterioration rate γ is obtained by the light-source deterioration correction apparatus 117 to apply the pulse beam 112 whose irradiation wavelength is set to 360 nm by the irradiation wavelength selection apparatus 116 from the irradiation head 115 to the leakage oil 139. The leakage oil 139 absorbs the pulse beam 112 and emits fluorescence.

Then, the fluorescence of the leakage oil 139 is observed by the photomultiplier 123 of the observation apparatus 120 in which the observation wavelength of the observation filter 121 is set to 400–450 nm.

The detection signal detecting the fluorescence of the leakage oil 139 observed by the photomultiplier 123 of the observation apparatus 120 is transmitted to the processing apparatus 130. The processing apparatus 130 generates a correction detection signal by computing the deterioration rate γ obtained by the light-source deterioration correction apparatus 117 for the detection signal. Thereby, it is possible to improve the deterioration of the film thickness measurement accuracy due to the deterioration of the pulse beam source 111. Moreover, only correction detection signals, while the leakage oil 139 fluoresces after irradiation of the pulse beam 112, are extracted. Each correction detection signal is obtained every ⅓ sec because the repetition cycle of the pulse beam source 111 is set to 3 Hz and successively sent to the signal integration apparatus 118. Then, a leakage-oil detection signal is obtained by integrating the correction detection signals up to the number of times of integration by the signal integration processing apparatus 133. In this case, the number of times of integration can be optionally selected out of $2^0, 2^1, 2^2, \ldots, 2^7$, and $2^8$ and the leakage oil detection signal is shown by the following expression (6).

[Expression 6]

(Leakage oil detection signal)=(Integrated correction detection signal)/(Number of times of integration)  (6)

By obtaining the leakage oil detection signal, it is possible to reduce the influence of an erroneous detection signal because of the effect of integration even if a high-intensity temporally-random disturbance with a luminescence wave length close to the fluorescence wavelength of the oil is detected in addition to the detection signal of the oil and the erroneous detection signal is observed. The leakage oil detection signal is sent to the film thickness computing apparatus 133 to obtain a film thickness from the previously stored film thickness computing conditions and the expression (1).

As the result of the above functions, the leakage oil is decided by a leakage oil detection signal obtained by integrating correction detection signals up to the set number of times. Therefore, it is possible to reduce the influence of an erroneous detection signal by the integration effect even if a high-intensity temporally-random disturbance with a luminescence wavelength close to the fluorescence wavelength of the oil is detected in addition to fluorescence of the oil and the erroneous detection signal is observed.

Further, the output monitor 135 is able to display the set number of times of integration and a leakage oil detection signal according to necessity.

Figure 22:
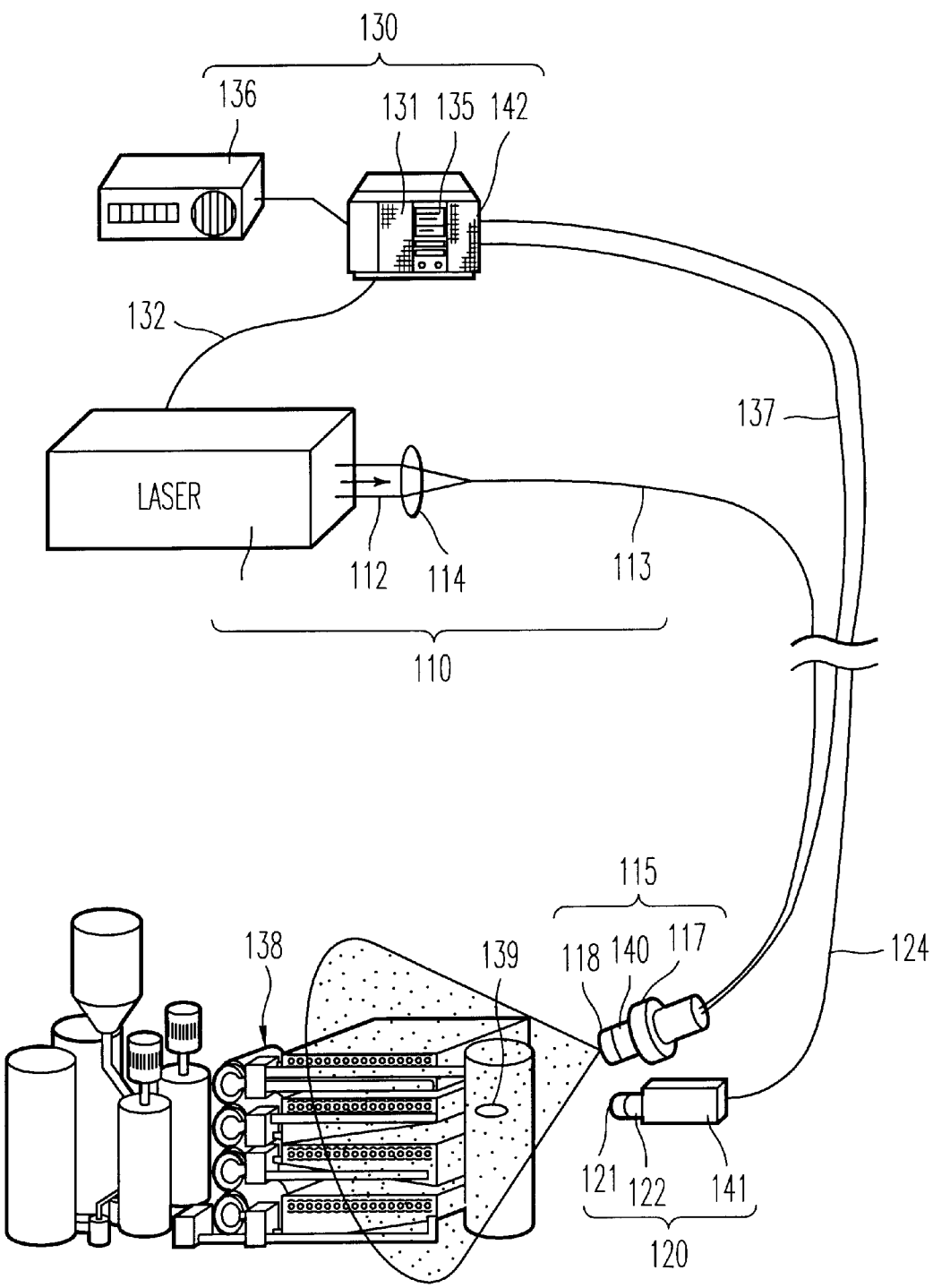
FIG. 22 is a view showing a structural arrangement of an oil detecting system according to a fourth embodiment of the present invention.

FIG. 22 shows an arrangement of a fourth embodiment of the oil detecting system according to the present invention, in which like reference numerals are added to portions or members corresponding to those mentioned with reference to the third embodiment.

In FIG. 22, the oil detecting system comprises an irradiation apparatus 110, an observation apparatus 120, and a processing apparatus 130. The irradiation apparatus 110 comprises a pulse beam source 111, a lens 114 for introducing the applied pulse beam 112 into a throttle optical fiber 1113 an optical fiber 113 for transmitting the introduced pulse beam 112 up to the vicinity of a monitoring region, and an irradiation head 115 for irradiating a purposed monitoring region with the pulse beam 112. The irradiation head 115 comprises a light-source deterioration correction apparatus 117 for correcting a film-thickness measurement accuracy by measuring the irradiation intensity of the pulse beam 112, an irradiation lens 119 for irradiating a monitoring region with the pulse beam 106 by enlarging the pulse beam 112 transferred through the optical fiber 113 up to the size of the monitoring region, and a wavelength selection device 140 with a curved surface for selecting an irradiation wavelength from the pulse beam 112.

The observation apparatus 120 comprises an observation filter 121 serving as a wavelength selection device for selecting and observing the luminescence wavelength of the oil, a lens 122 for adjusting a region to be observed to a monitoring region and an avalanche photodiode 141 for observing the fluorescence of the oil.

The processing apparatus or processor 130 comprises a timing controller 131 for controlling the irradiation timing of the pulse beam source 111, a timing signal transmission line 132 for transmitting a timing signal output from the timing controller 131 to the pulse beam source 111, a film thickness computing apparatus 142 for integrating output signals of the avalanche photodiode 141 and computing the film thickness of the leakage oil in accordance with the number of times of integration and an alarm 136 for communicating the presence or absence of the oil leakage to persons.

In this embodiment, it is assumed that the leakage oil 139 to be detected is gas turbine oil and the oil leaks from a unit under normal illumination by a fluorescent lamp or the like.

Functions and advantages of the present embodiment will be described hereunder.

The pulse beam source 111 uses a Xe flash lamp similarly to the above case. It is assumed that an irradiation wavelength includes the absorption wavelength of the leakage oil 139 to be detected and has a wavelength which excites the leakage oil 139 and makes it luminesce and whose fluorescence intensity is proportional to a film thickness. Thus, the expression (1) showing the relation between the excited light absorbed by an oil with a film thickness d and fluorescence emitted by the excited light is approximated as shown by the following expression (7).

[Expression 7]

$$I_f = \frac{I_a \cdot \alpha}{\beta}(1 - e^{-\beta d}) \quad (7)$$

$$= \frac{I_a \cdot \alpha}{\beta}\left(1 - \left[1 + \frac{(-\beta \cdot d)^1}{1!} + \frac{(-\beta \cdot d)^2}{2!} + \frac{(-\beta \cdot d)^3}{3!} \cdots\right]\right)$$

$$\approx \frac{I_a \cdot \alpha}{\beta} \cdot \beta \cdot d$$

$$= I_a \cdot \alpha \cdot d$$

$I_a$: Excited light intensity, $I_f$: Fluorescence intensity, $\alpha$: Fluorescence efficiency, $\beta$: Absorption coefficient In this case, the fluorescence intensity $I_f$ is proportional to the film thickness d. Moreover, it is to be noted that the above approximate expression (7) is established in case the following expression (8) be effected.

[Expression 8]

$$d \ll 1 \quad (8)$$

A purposed measurement range is assumed as 0 to 100 μm to select the value β meeting the expression (8) under the condition of $0 \leq d \leq 10^4$. It is possible to set β to any value. In this case, β is set to $10^2$.

$\beta = 10^2$ is substituted for the expression (4) to obtain an absorbance and select a wavelength meeting the absorbance out of the absorption wavelengths of the gas turbine oil to be detected shown in FIG. 3. Absorbance A is obtained from the expression (4) as shown below.

Expression 9

$$A = \beta c L = 10^2 \; 0.0026 \; 0.01 = 0.0026 \quad (9)$$

c: Oil concentration (c=0.0026), L: Optical path length (L=0.01 m)

Moreover, by selecting a wavelength allowing the absorbance A to be set to 0.0026 out of the absorption wavelengths shown in FIG. 3, it is possible to determine that it is preferable to set an irradiation wavelength to approximately 380 nm. Therefore, to measure gas turbine oil with a film thickness of 0 to 100 μm, it is necessary to set the irradiation wavelength to 380 nm. Furthermore, the fluorescence intensity of the leakage oil decision film thickness to be decided as leakage oil is stored in the film thickness computing apparatus 142 as a reference fluorescence intensity value.

Table 2 shows irradiation wavelengths obtained to measure film thicknesses from 0 to 100 μm of various types of oils according to the same procedure as the above.

TABLE 2

Irradiation Wavelength used for Measurement of Oil Film Thickness 100 μm

| Type of Oil | Irradiation Wavelength (nm) |
| --- | --- |
| Gas turbine oil | 380 |
| Steam turbine oil | 330 |
| High-pressure hydraulic oil | 300 |

According to Table 2, wavelength selection devices allowing an irradiation wavelength to be set to 300, 330, and 380 nm are provided for the irradiation wavelength selection device 140. Further, similarly, reference fluorescence intensity values of various oils to be decided as leakage oil are stored in the film thickness computing apparatus 142.

As the result of the above functions, it is possible to obtain the relation that a fluorescence intensity is proportional to a film thickness as shown in the expression (8) by selecting the irradiation wavelength of the pulse beam 105 to 380 nm and making fluoresce the leakage oils of the gas turbine oil, steam turbine oil, and high-pressure hydraulic oil with a film thickness of 0 to 100 μm.

Then, the functions and advantages of the wavelength selection device 140 according to the second embodiment are described below.

To detect the leakage oil 139 of gas turbine oil leaking from a unit under normal illumination by a fluorescent lamp or the like shown in FIG. 22, the pulse beam source 111 is made to luminesce at 3 Hz similarly to the above described case. The pulse beam 112 emitted from the pulse beam source 111 is throttled by the lens 114 and enters the optical fiber 113. The pulse beam 112 is led to the irradiation head 115 by the optical fiber 113. The irradiation head 115 first obtains the deterioration rate γ by the light-source deterioration correction apparatus 117 in order to improve a deteriorated measurement accuracy.

Then, an irradiation wavelength of the pulse beam 112 suitable for the type of the leakage oil is selected by the curved-surface wavelength selection device 140 to apply the pulse beam 112 to the leakage oil. Because the leakage oil 139 is gas turbine oil, the wavelength selection device 140 allowing the irradiation wavelength to be set to 380 nm is selected. In this case, because the wavelength selection device 140 is constituted so as to have a curved surface, all angular components of the pulse beam 112 emitted from the optical fiber 113 to expand in the irradiation head always vertically enter the wavelength selection device 140. The wavelength selection device has a characteristic in which a selected wavelength is deviated from a purposed wavelength unless a beam vertically enters the wavelength selection device. Therefore, when using a flat wavelength selection device, because there are some angular components of the pulse beam 112 emitted from the optical fiber 113 expanding but not vertically entering the wavelength selection device, a selected wavelength is changed due to an irradiation angle.

As the result of the above functions, by using the curved-surface wavelength selection device 140, the selected wavelength of the wavelength selection device is changed due to the incident angle of the pulse beam 112 and thereby, it is possible to remove the angle dependency of an irradiation wavelength caused by the above selected wavelength change that the irradiation wavelength of the irradiation head 115 is changed due to the irradiation wavelength and set the irradiation wavelength to 380 nm uniformly in any direction. The curved-surface wavelength selection device 140 uses, for example, a colored-glass filter or interference filter.

Then, the functions and advantages of the avalanche photodiode 141 and film thickness computing device 142 of the present embodiment will be described hereunder.

The leakage oil 139 absorbs a pulse beam emitted from the irradiation head 115 and emits fluorescence. The fluorescence, as described above, has the luminescence wavelength shown in FIG. 13 and the luminous period shown in FIG. 8. Therefore, the avalanche photodiode 141 of the observation apparatus 120 in which the observation wavelength of the observation filter 121 is set to 400 to 450 nm is gate-operated by the timing controller 131 to observe fluorescence only for 200 ns after irradiation of a pulse beam.

A detection signal observed by the avalanche photodiode 141 of the observation apparatus 120 is transmitted to the processor 130. The processor 130 generates a correction detection signal by computing the deterioration rate obtained by the light-source deterioration correction apparatus 111 for the detection signal. Thereby, it is possible to improve a film-thickness measurement accuracy degraded due to deterioration of the pulse beam source 111. Each correction detection signal is obtained every ⅓ sec because the repetition cycle of the pulse beam source 111 is set to 3 Hz and successively sent to the film thickness computing apparatus 142.

The film thickness computing apparatus 142 integrates the correction detection signals to compute a fluorescence intensity for each number of times of integration. The integration is performed until a fluorescence-intensity measured value reaches a previously-stored reference fluorescence intensity value to obtain the number of times of integration. A film thickness is obtained by using the number of times of integration and using the fact that a film thickness is proportional to a fluorescence intensity in accordance with the following expression (10).

[Expression 10]

(Film thickness)=(Film thickness at reference fluorescence intensity value)/(Number of times of integration) (10)

The presence or absence of the leakage oil is decided in accordance with the film thickness and leakage oil is decided when a preset leakage-oil decision film thickness is obtained. The output monitor 135 is able to display the presence or absence of leakage oil, film thickness, number of times of integration, correction detection signal, or reference fluorescence intensity value and its film thickness according to necessity. Moreover, it is possible to communicate the presence or absence of the leakage oil to persons by turning on a warning lamp or outputting sounds by the alarm 136.

As the result of the above functions, by selecting an observation wavelength by the observation filter 121, gate-operating the avalanche photodiode 141, and observing the fluorescence of oil only for a certain period after irradiation of a pulse beam, it is possible to select and observe the luminescence wavelength of the oil only for the luminous period even if there is a disturbance such as a fluorescent lamp or luminescence of a background unit. Moreover, by selecting an irradiation wavelength for the expression (7) to be effected, it is possible to make the fluorescence of oil proportional to a film thickness. Furthermore, by integrating the signals detected by the avalanche photodiode 141 until their level reaches a previously-stored fluorescence intensity value and obtaining the number of times of integration, it is possible to compute the film thickness of leakage oil in accordance with the expression (10).

The fifth embodiment of the present invention will be described hereunder with reference to FIG. 23.

Figure 23:
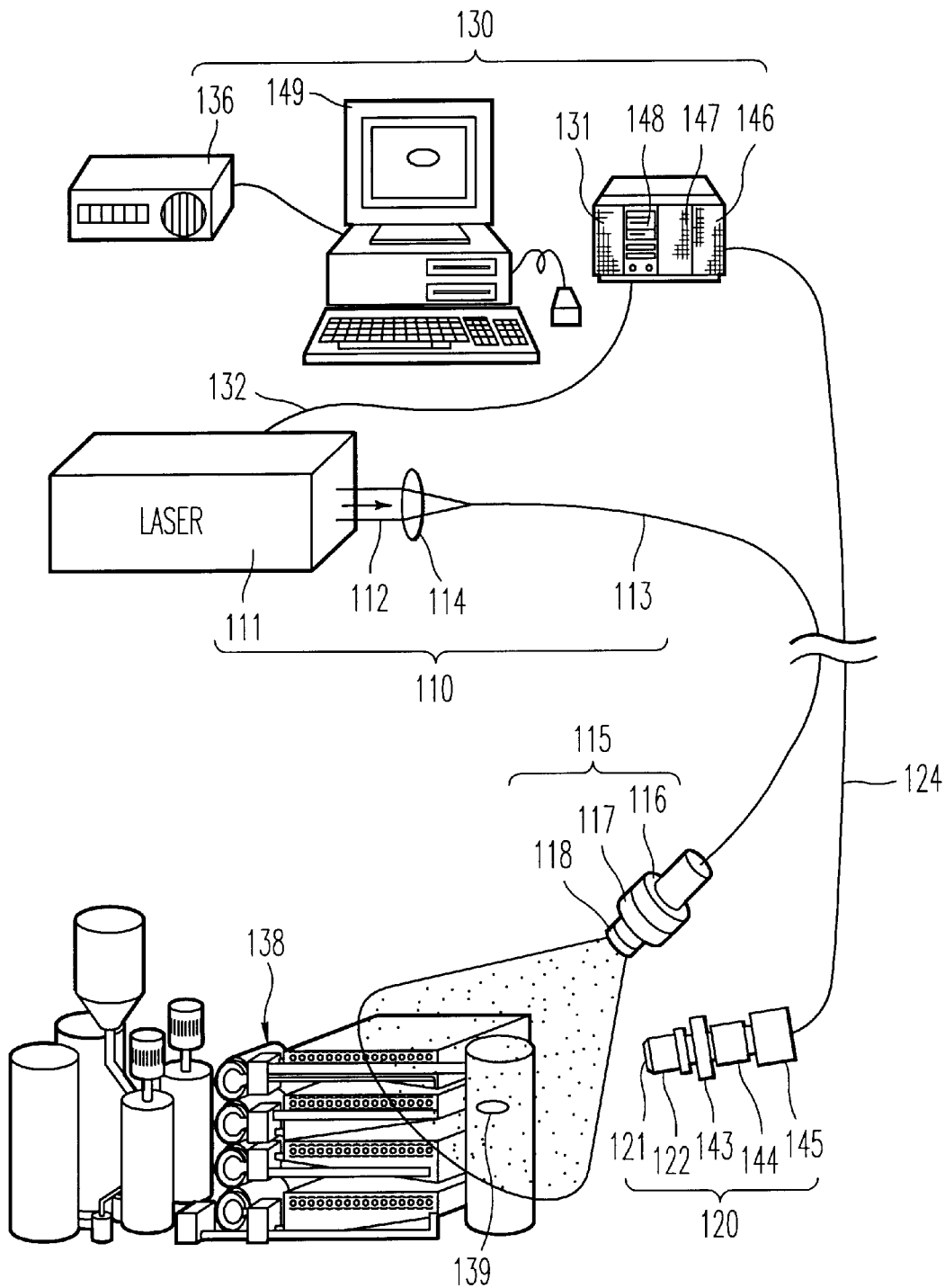
FIG. 23 is a view showing a structural arrangement of an oil detecting system according to a fifth embodiment of the present invention.

In FIG. 23, the leakage oil detector comprises an irradiation apparatus 110, an observation apparatus 120, and a processing apparatus or processor 130. The irradiation apparatus 110 comprises a pulse beam source 111, a lens 114 for introducing an irradiated pulse beam 112 from the pulse beam source 111 into a throttle optical fiber 113, an optical fiber 113 for transmitting the introduced pulse beam 112 up to the vicinity of a monitoring region, and an irradiation head 115 for irradiating a purposed monitoring region with the pulse beam 112. The irradiation head 115 comprises an irradiation wavelength selection apparatus 116 provided with a plurality of wavelength selection devices and capable of selecting the irradiation wavelength of the pulse beam 112, a light-source deterioration correction apparatus 117 for correcting a film-thickness measurement accuracy by measuring the irradiation intensity of the pulse beam 112, and an irradiation lens 118 for irradiating the pulse beam 112 by enlarging the beam 112 through the optical fiber 113 up to the size of a monitoring region.

The observation apparatus 120 comprises an observation filter 121 serving as a wavelength selection device for selecting and observing the fluorescence wavelength of oil, a lens 122 for adjusting a region to be observed to a monitoring region, a fast-gate-provided image intensifier 143 having fast-shutter function and image-intensifying function for selecting only the luminous period of oil to observe it, an image fiber 144 for image-transmitting a fluorescent image of the oil observed by the fast-gate-provided image intensifier 143, and a CCD camera 145 for monitor-displaying an image transmitted by the image fiber 144. The processor 130 comprises a timing controller 131 for controlling the irradiation timing of the pulse beam source 111 and the shutter timing of the fast-gate-provided image intensifier 143 and selecting only the period in which oil luminesces after irradiation of the pulse beam 112 to observe the luminescence, a timing signal transmission line 132 for transmitting a timing signal sent from the timing controller 131 to the pulse beam source 111, an image integration apparatus 146 for integrating an image output from the CCD camera 145, a film thickness distribution computing apparatus 147 for computing the film thickness distribution of the leakage oil by correcting the fluorescence intensity of the oil in accordance with the information for the distance between a monitoring object and an oil detector, an oil quantity computing apparatus 148 for obtaining the quantity of leakage oil, an image monitor 149 for displaying the integration result of the image integration apparatus 146, film thickness distribution obtained by the film thickness distribution computing apparatus 147 and the leakage oil quantity obtained by the oil quantity computing apparatus 148, and an alarm 136 for communicating presence or absence of leakage oil to persons.

It is assumed that the leakage oil 139 to be detected is gas turbine oil and leaks from a unit under normal illumination by a fluorescent lamp or the like.

Functions and advantages of the fifth embodiment will be described hereunder.

The pulse beam source 111 uses a Xe flash lamp similarly to the above described case and it is made to luminesce at 3 Hz by the timing controller 131. A pulse beam emitted from the pulse beam source 111 is throttled by the lens 114 and enters the irradiation head 115. The pulse beam is led to the irradiation head 115 by the optical fiber 113. The irradiation head 115 first selects an irradiation wavelength. Because the leakage oil 139 uses gas turbine oil, the irradiation wavelength is set to 380 nm by the wavelength selection device of the irradiation wavelength selection apparatus 116. Moreover, to improve a degraded measurement accuracy due to deterioration of the pulse beam source 111, a deterioration rate is determined by the light-source deterioration correction apparatus 117. Thereafter, the pulse beam is adjusted to an optional size in accordance with the size of a monitoring region and emitted. The leakage oil 139 absorbs the pulse beam emitted from the irradiation head 115 and fluoresces. The fluorescence has the luminescence wavelength shown in FIG. 13 and the luminous period shown in FIG. 8. Therefore, the fluorescence of the leakage oil 139 is observed by setting the observation wavelength of the observation filter 121 to 400 to 450 nm and shutter-operating the fast-gate-provided image intensifier 143 only for a period of 200 ns after irradiation of the pulse beam.

As the result of the above functions, by selecting the luminescence wavelength of oil and performing observation only for the luminous period by the observation filter 121 and fast-gate-provided image intensifier 143, it is possible to selectively observe only the fluorescence of the oil even if there is a disturbance such as a fluorescent lamp or the like or luminescence of a background, unit. A detection image of leakage oil observed by the fast-gate-provided image intensifier is image-transmitted by the image fiber 144 and picked up by the CCD camera 145. Thereafter, the detection image is sent to the processor 130 as an image signal.

The processor 130 first generates a corrected detection image by computing the deterioration rate obtained by the light-source deterioration correction apparatus 117 for the detection image. Thereby, it is possible to improve a degraded film-thickness measurement accuracy due to deterioration of the pulse beam source 111. Each corrected detection image is obtained every ⅓ sec because the repetition cycle of the pulse beam source 111 is set to 3 Hz and successively sent to the image integration apparatus 146. Moreover, a leakage oil detection image is obtained by integrating the corrected detection image up to the number of times of integration by the image integration apparatus 146. In this case, the number of times of integration can be optionally changed between 1 and 28 times and the leakage oil detection image is shown by the following expression (11).

[Expression 11]

(Leakage-oil detection image)=(Integrated, corrected detection images)/(Number of times of integration) (11)

As the result of the above functions, by obtaining the leakage oil detection image, it is possible to reduce the influence of an erroneous detection image by the effect of integration even if detecting a high-intensity temporally-random disturbance whose luminescence wavelength is close to the fluorescence wavelength of oil in addition to an oil detection image and observing the erroneous detection image.

Then, the functions and advantages of the film thickness distribution computing apparatus of the fifth embodiment are described below.

In the case of a leakage oil detection image, the position of each pixel is shown by a horizontal axis x and a vertical axis y so that the following inequalities are effected: $1 \leq x \leq X$ and $1 \leq y \leq Y$ (X: maximum value of a pixel in a horizontal direction of the image monitor 149 and Y: maximum value of a pixel in a vertical direction thereof). A film thickness distribution is obtained from the fluorescence intensity distribution of the leakage oil detection image. However, if an actual monitoring portion corresponding to a pixel (x,y) is changed, the film thickness distribution cannot be easily obtained from the fluorescence intensity of each pixel because the distance up to the observation apparatus 120 and the intensity of a pulse beam to be irradiated differ.

Therefore, because the film thickness distribution is obtained by correcting the fluorescence intensity, detection distance conditions and reference film thickness conditions are stored in the film thickness distribution computing apparatus 129. The detection distance conditions include the distance $L_p$ (x,y) between the monitoring portion corresponding to a pixel (x,y) and the irradiation head 115 and the distance $L_o$ (x,y) between the monitoring portion and the observation apparatus 120. The reference film thickness conditions include the excited light intensity $I_a$, fluorescence efficiency $\alpha$ and absorption coefficient $\beta$ at the reference distance $L_{p\ b}$ between the monitoring portion and the irradiation head 115 and the reference distance $L_{o\ b}$ (x,y) between the monitoring portion and the observation apparatus 120. Moreover, the fluorescence intensity distribution $I_f(x,y)$ is obtained from the fluorescence intensity I(x,y) of each pixel in accordance with the following expression (12).

[Expression 12]

$$I_f(x, y) = I(x, y) \cdot \frac{L_{pb}^2}{L_p(x, y)^2} \cdot \frac{L_{ob}^2}{L_o(x, y)^2} \quad (12)$$

In the case of the expression (12), the fluorescence intensity distribution $I_f(x,y)$ is obtained by using the fact that the pulse beam irradiation intensity at a monitoring portion is inversely proportional to the square of distance and the fluorescence intensity generated by irradiation of the pulse beam is also inversely proportional to the square of distance. Thus, the film thickness distribution F(x,y) is obtained from the fluorescence intensity distribution $I_f(x,y)$ and the expression (1).

As the result of the above functions, it is possible to obtain the fluorescence intensity distribution $I_f(x,y)$ by correcting the fluorescence intensity of a detection image in accordance with the information for the distance between a monitoring object and an oil detector.

Then, the functions and advantages of the oil quantity computing apparatus 148 of this fifth embodiment are described hereunder.

A leakage oil quantity is obtained by the oil quantity computing apparatus 148. First, the fluorescent region of leakage oil is extracted from a leakage oil detection image to obtain S(x,y) defined by the following expression (13) in accordance with the inequalities 1≦x≦X and 1≦y≦Y.
[Expression 13]

$$S(x, y) = \begin{bmatrix} C & \text{(Area per one pixel in monitoring portion)} \\ O & \end{bmatrix} \quad (13)$$

Then, the leakage oil quantity V is computed in accordance with the following expression (14).
[Expression 14]

$$V = \sum_{x,y} F(x, y) \times S(x, y) \quad (1 \leq x \leq X, 1 \leq y \leq Y) \quad (14)$$

Moreover, the area D of leakage oil can be computed in accordance with the following expression (15).
[Expression 15]

$$D = \sum_{x,y} S(x, y) \quad (1 \leq x \leq X, 1 \leq y \leq Y) \quad (15)$$

As the result of the above functions, by the oil quantity computing apparatus 148, it is possible to obtain the leakage oil quantity shown by the expression (14) and the area of leakage oil shown by the expression (15) by computing the film thickness distribution obtained by the film thickness distribution computing apparatus 147 and the fluorescent region extracted from the leakage oil detection image.

Moreover, it is possible to decide the presence or absence of the leakage oil from any one of the film thickness distribution F(x,y), area D, and quantity V of leakage oil. In any case, it is possible to decide leakage oil when it exceeds a set value. It is possible to successively monitor the leakage oil detection images by the image monitor 149 for displaying an image. At the same time, it is possible to display the film thickness distribution F(x,y), area D, and quantity V of the leakage oil. Moreover, it is possible to communicate the presence or absence of the leakage oil to persons by turning on a warning lamp or outputting sounds by the alarm 136 for communicating the presence of the leakage oil to persons.

Furthermore, because the film thickness distribution F(x, y), area D, and leakage quantity of oil can be obtained, it is possible to monitor the oil coated and lubricating states by monitoring a lubricating portion of a unit or vehicle under manufacture or operation.

The sixth embodiment of the present invention will be described hereunder with reference to FIG. 24.

Figure 24:
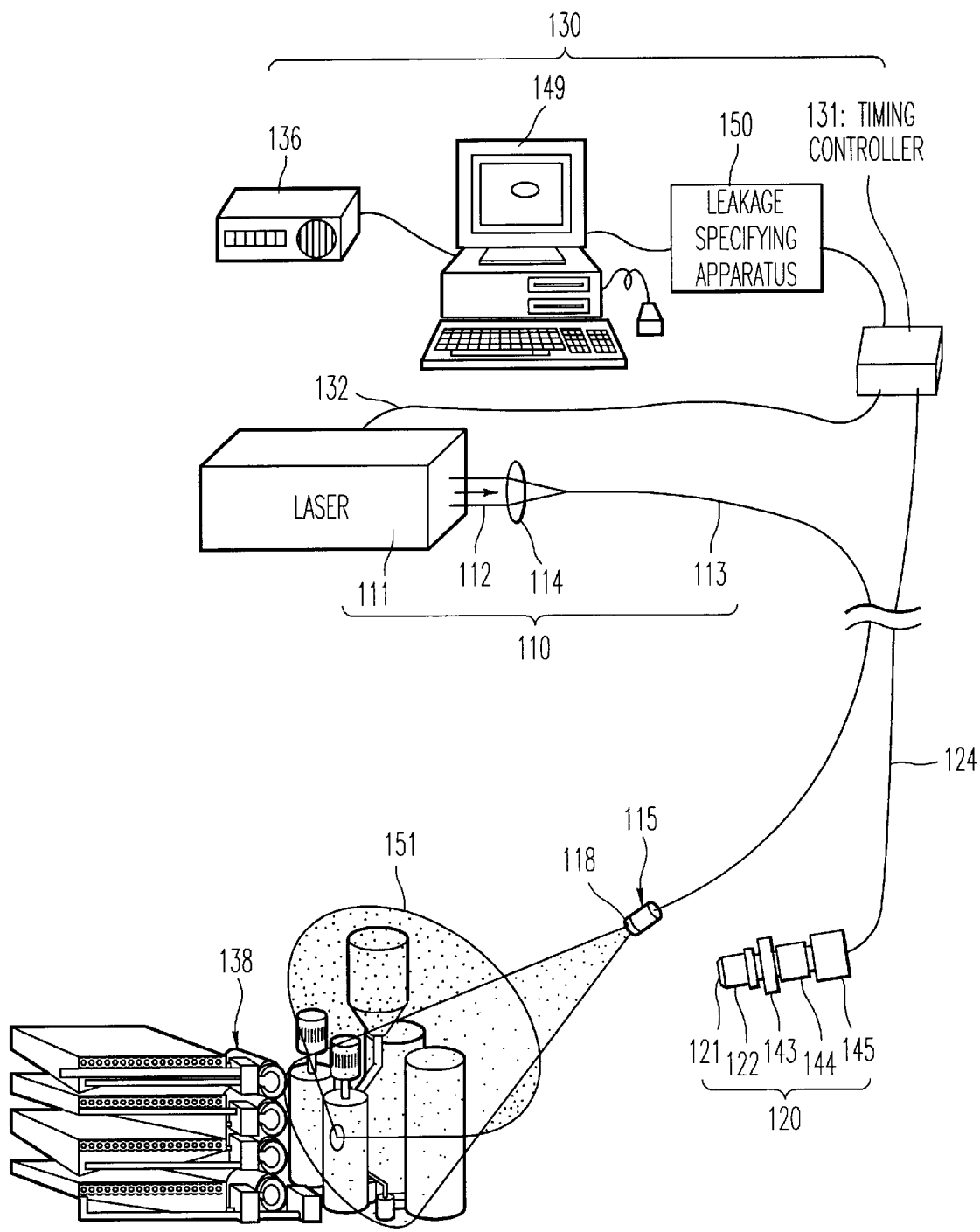
FIG. 24 is a view showing a structural arrangement of an oil detecting system according to a sixth embodiment of the present invention.

In FIG. 24, the leakage oil detecting system comprises, likely in the former embodiments, an irradiation apparatus 110, an observation apparatus 120, and a processor 130. The irradiation apparatus 110 comprises a pulse beam source 111, a lens 114 for throttling an irradiated pulse beam 112 and introducing it to an optical fiber 113, an optical fiber 113 for transmitting the introduced pulse beam 112 up to the vicinity of a monitoring region, and an irradiation head 115 for irradiating a purposed monitoring region with the pulse beam 112. The irradiation head 115 comprises an irradiation lens 118 for irradiating the monitoring region by enlarging the pulse beam 112 to the size of the monitoring region.

The observation apparatus 120 comprises an observation filter 121 serving as a wavelength selection device for selecting and observing the luminescence wavelength of oil, a lens 122 for adjusting a region to be observed to a monitoring region, a fast-gate-provided image intensifier 143 having fast-shutter function and image-intensifying function for selecting only the luminous period of oil for observation, an image fiber 144 for image-transmitting the fluorescent image of the oil observed by the fast-gate-provided image intensifier 143, and a CCD camera 145 for monitor-displaying an image transmitted by the image fiber 144.

The processor 130 comprises a timing controller for controlling the irradiation timing of the pulse beam source 111 and the shutter timing of the fast-gate-provided image intensifier 143 to select and observe only the period in which the oil after irradiated with the pulse beam 112 luminesces, a timing signal transmission line 132 for transmitting a timing signal from the timing controller 131 to the pulse beam source 111, an oil leakage portion specifying apparatus 150 for specifying an oil leakage portion in accordance with the temporal change of observed oil particles, an image monitor 149 for image-displaying the oil leakage portion specified by the oil leakage portion specifying apparatus 150, and an alarm 136 for communicating the presence or absence of oil leakage to persons.

For oil leakage, a case is assumed in which steam turbine oil is scattered in the form of foggy fine particles from a unit under normal illumination by a fluorescent lamp or the like. The foggy leakage oil 151 may occur when the oil used for high-pressure operations of a unit in a plant leaks.

Functions and advantages according to the sixth embodiment will be described hereunder.

The pulse beam source 111 uses a pulse laser. The pulse laser is determined in accordance with a luminescence wavelength. The luminescence wavelength must be a wavelength which contains the absorption wavelength of the foggy leakage oil 151 to be detected and excite the foggy leakage oil 151 to make it luminesce. Therefore, judging from the absorption wavelengths of various oils shown in FIGS. 2, 5, 15 and 13, it is found that the luminescence wavelength of the pulse laser must be kept in an ultraviolet range between 200 and 280 nm in order to excite all types of oils to make them luminesce. Moreover, because a monitoring region expands, it is preferable that the pulse laser has a high output and its laser beam is a short pulse so that it does not become a disturbance. From the viewpoints of the luminescence wavelength, output, and pulse, it is possible to use a titanium-sapphire laser, excimer laser, or YAG laser as a pulse beam source usable for the oil detector. In this case, the pulse beam source 111 uses the fourth harmonic of the YAG laser (luminescence wavelength of 266 nm, pulse width of 5 ns: FWHM).

The foggy leakage oil 151 of steam turbine oil is detected from a unit under normal illumination by a fluorescent lamp or the like shown in FIG. 24 by the observation apparatus 120 in which the observation wavelength of the observation filter 121 is set to 350 to 400 nm in accordance with the luminescence wavelength of the steam turbine oil shown in FIG. 12. The pulse beam source 111 is made to luminesce by the timing controller 131. Because the repetition cycle in the above case can be optionally determined in accordance with a time interval to be monitored, it is set to 10 Hz. The pulse beam 112 emitted from the pulse beam source 111 is throttled by the lens 114 and enters the optical fiber 113. The pulse beam is led to the irradiation head 115 by the optical fiber 113. The irradiation head 115 applies the pulse beam to a monitoring region by adjusting the beam to an optional size in accordance with the size of the region. The foggy leakage oil 151 absorbs the pulse beam emitted from the irradiation head 115 to emit fluorescence. The fluorescence has the luminescence wavelength shown in FIG. 12 and the luminous period shown in FIG. 7. Therefore, the fast-gate-provided image intensifier 143 of the observation apparatus 120 is shutter-operated by the timing controller 131 only for a period of 200 ns after irradiation of the pulse beam. Thus, by selecting the luminescence wavelength of oil only to perform observation only for the luminous period by the observation filter 121 and fast gate-provided image intensifier 143, it is possible to selectively observe only the fluorescence of the oil even if there is a disturbance by a fluorescent lamp or the like or luminescence of a unit. A leakage oil detection image observed by the fast-gate-provided image intensifier 143 is image-transmitted by the image fiber 144 and picked up by the CCD camera 145. Each detection image is obtained every 1/10 sec because the repetition cycle of the pulse beam source 111 is set to 10 Hz and successively sent to the oil leakage portion specifying apparatus 150 of the processor 130 as an image signal.

The oil leakage- portion specifying apparatus 150 specifies an oil leakage portion in accordance with the temporal change of the detection image transmitted every 1/10 sec. Because the detection image is the foggy leakage oil 151, it appears as an image in which numberless small oil particles emit fluorescence. Therefore, a detection image is compared with a detection image 1/10 sec later. By comparing both the images each other, it is possible to obtain the moving direction of each oil particle in accordance with its trace. Moreover, by following up the moving origin of each oil particle, it is possible to specify an oil leakage portion of a unit.

Moreover, detection images can be successively monitored by the image monitor 149 for displaying an image. A detection image in which only leakage oil fluoresces can be obtained by the image monitor 149 and moreover, early detection is realized because even a very small quantity of leakage oil can be detected when it fluoresces. Furthermore, it is possible to communicate leakage oil to persons by turning on a warning lamp or outputting sounds by the alarm 136 for communicating the presence of the leakage oil to persons.

As the result of the above functions, it is possible to select and observe only the fluorescence of oil by selecting the luminescence wavelength of oil and observing it only for the luminous period by the observation filter 121 and the fast-gate-provided image intensifier 143 even if there is a disturbance by a fluorescent lamp or the like or luminescence of a unit.

Because a detection image appears as an image in which numberless small oil particles fluoresce, it is possible to specify an oil leakage portion of a unit by comparing the detection image with a detection image a certain time later and thereby, computing the moving direction of each foggy oil particle and following up the moving origin.

Figure 25:
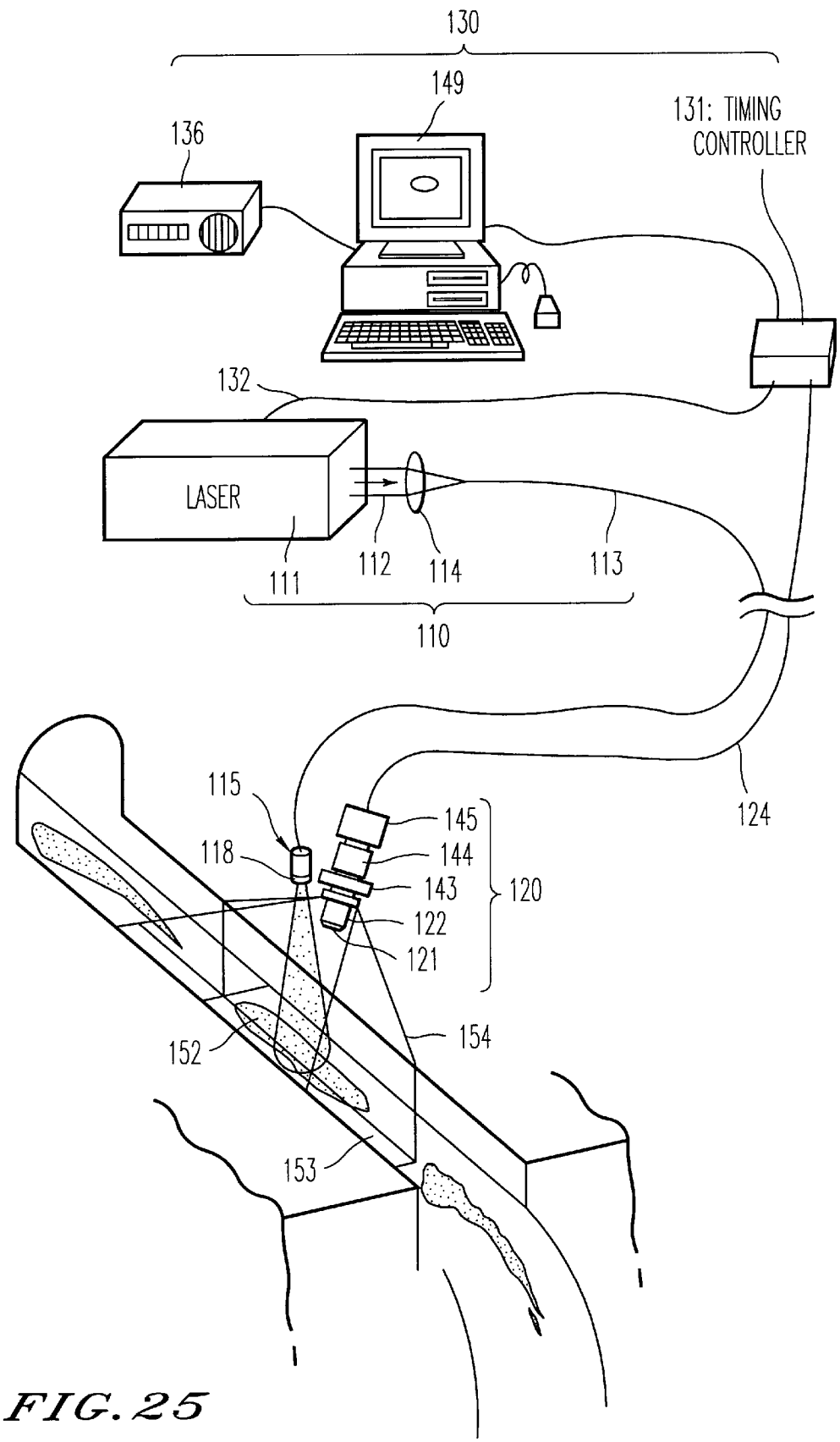
FIG. 25 is a view showing a structural arrangement of an oil detecting system according to a seventh embodiment of the present invention.

The seventh embodiment of the present invention is described hereunder with reference to FIG. 25.

In FIG. 25, the leakage oil detecting system comprises, as like in the former embodiments, an irradiation apparatus 110, an observation apparatus 120, and a processor 130. The irradiation apparatus 101 comprises a pulse beam source 111, a lens 114 for throttling an irradiated pulse beam 112 and introducing it to an optical fiber 113, an optical fiber 113 for transmitting the introduced pulse beam 112 up to the vicinity of a monitoring region, and an irradiation head 115 for irradiating a purposed monitoring region with the pulse beam 112. The irradiation head 115 comprises an irradiation lens 118 for irradiating the monitoring region by enlarging the pulse beam 112 to the size of the monitoring region.

The observation apparatus 120 comprises an observation filter 121 serving as a wavelength selection device for selecting and observing the luminescence wavelength of oil, a lens 122 for adjusting a region to be observed to a monitoring region, a fast-gate-provided image intensifier 143 having fast-shutter function and image-intensifying function for selecting only the luminous period of oil for observation, an image fiber 144 for image-transmitting the fluorescent image of the oil observed by the fast-gate-provided image intensifier 143, and a CCD camera for monitor-displaying an image transmitted by the image fiber 144.

The processor 130 comprises a timing controller for controlling the irradiation timing of the pulse beam source 111 and the shutter timing of the fast-gate-provided image intensifier 143 to select and observe only the period in which the oil after irradiated with the pulse beam 112 luminesces, a timing signal transmission line 132 for transmitting a timing signal from the timing controller 131 to the pulse beam source 111, an image monitor 149 for image-displaying an oil leakage state, and an alarm 136 for communicating the presence or absence of oil leakage to persons.

It is assumed that a leakage oil to be detected is steam turbine oil discharged from a water outlet of a plant or building. The oil discharged from the water outlet is a very-thin oil film with a thickness of several microns, which is frequently discharged in the form of a thin-film leakage oil 152 floating on the surface of waste water. Therefore, to improve the detection sensitivity of the leakage oil detector, a reflector 153 for reflecting the fluorescence of leakage oil is set to the bottom of the water outlet at a monitoring portion so as to also observe the fluorescence of the leakage oil reflected at the bottom. The reflector 153 is fixed to a supporting member 154 secured to the front portion of the observation apparatus 120.

Functions and advantages of this seventh embodiment will be described hereunder.

The thin-film leakage oil 152 of steam turbine oil is detected from the water outlet shown in FIG. 25 by the oil detector of this embodiment. The pulse beam source 111 is made to luminesce by the timing controller 131. The repetition cycle of luminescence can be optionally determined in accordance with a time interval to be monitored and therefore, it is set to 10 Hz. The pulse beam 112 emitted from the pulse beam source 111 is throttled by the lens 114 and enters the optical fiber 113. The pulse beam is led to the irradiation head 115 by the optical fiber 113. The irradiation head 115 irradiates the pulse beam by adjusting to an optional size in accordance with the size of a monitoring region. The thin-film leakage oil 152 absorbs the pulse beam emitted from the irradiation head 115 to emit fluorescence. In this case, it is possible to observe the fluorescence reflected at the bottom of the water outlet by the reflector set to the bottom of the water outlet in addition to the fluorescence to be directly observed from the thin-film leakage oil 152. Therefore, it is possible to increase an observation luminous energy.

The fluorescence has the luminescence wavelength shown in FIG. 12 and the luminous period shown in FIG. 7. Therefore, the fluorescence of the thin-film leakage oil 152 is observed by setting the observation wavelength of the observation filter 113 to 350 to 400 nm and shutter-operating the fast-gate-provided image intensifier 143 of the observation apparatus 120 only for a period of 200 ns after irradiation of the pulse beam. Therefore, by increasing the observation luminous energy by the reflector 153 and selecting the luminescence wavelength of oil to perform observation only for the luminous period by the observation filter 121 and the fast-gate-provided image intensifier 143, it is possible to detect even a very small quantity of thin-film leakage oil at a high sensitivity even if there is reflected light of a fluorescent lamp or the like or other light serving as a disturbance on the water surface.

A leakage oil detection image observed by the fast-gate-provided image intensifier 143 is image-transmitted by the image fiber 144 and picked up by a CCD camera 145. Each detection image is obtained every $\frac{1}{10}$ sec because the repetition cycle of the pulse beam source 111 is set to 10 Hz and successively sent to the processor 130.

The processor 130 makes it possible to successively monitor detection images by the image monitor 149 for displaying an image. Because the image monitor 149 makes it possible to obtain a detection image in which only leakage oil fluoresces and moreover detect even a very small quantity of leakage oil if the leakage oil fluoresces, early detection is realized. Moreover, it is possible to communicate the presence of the leakage oil to persons by turning on a warning lamp or outputting sounds by the alarm 136.

As the result of the above functions, it is possible to observe the fluorescence reflected at the bottom of a water outlet by the reflector 153 set to the bottom of the water outlet in addition to the fluorescence to be directly observed from the thin-film leakage oil 152 and therefore, an observation luminous energy can be increased. Moreover, by selecting the luminescence wavelength of oil and observing the fluorescence of the thin-film leakage oil 152 only for the luminous period by the observation filter 121 and the fast-gate-provided image intensifier 143, it is possible to detect a very small quantity of the thin-film leakage oil 152 at a high sensitivity even if there is reflected light of a fluorescent lamp or the like or other light serving as a disturbance on the water surface.

The eighth embodiment of the present invention will be described hereunder with reference to FIG. 26.

Figure 26:
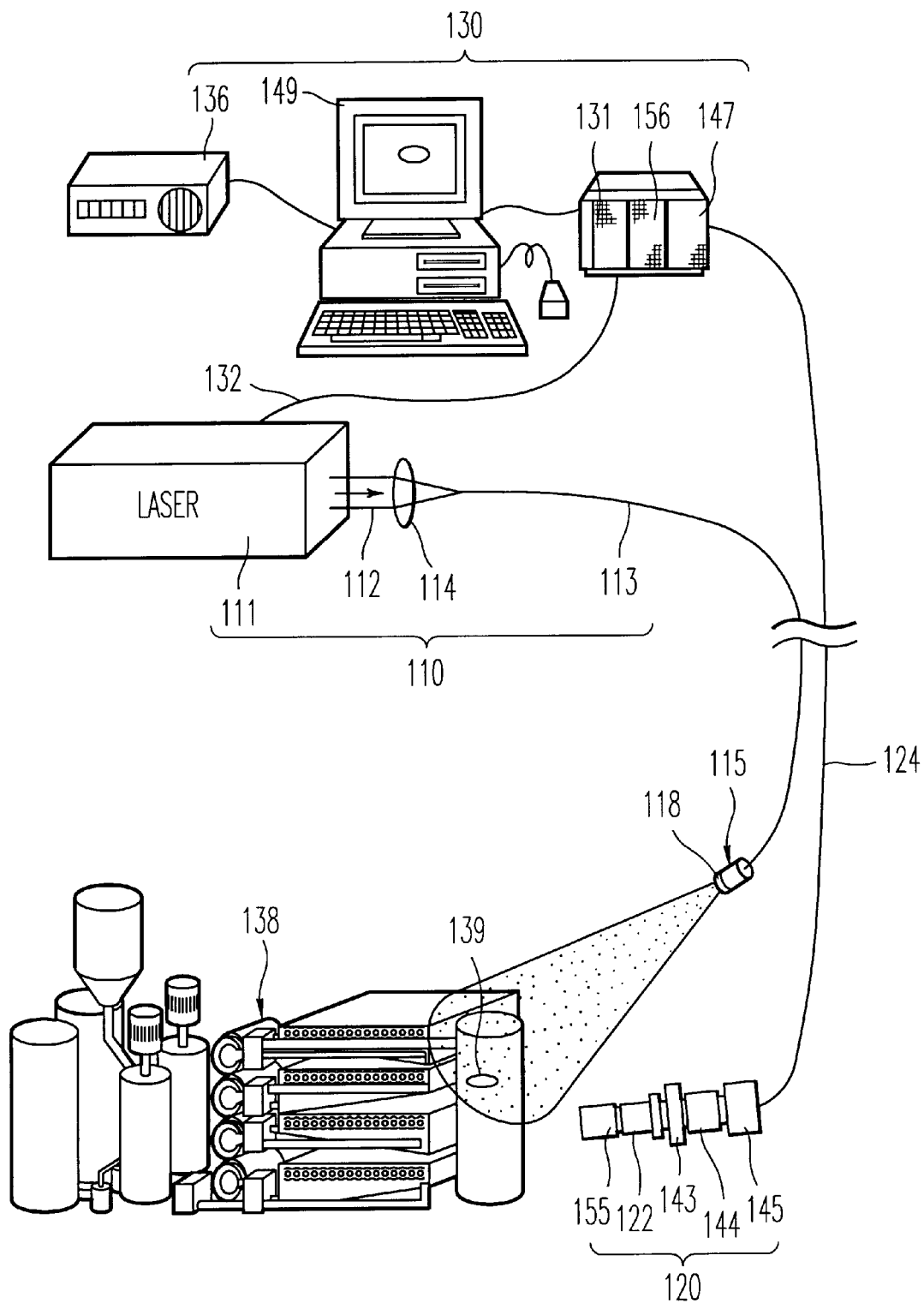
FIG. 26 is a view showing a structural arrangement of an oil detecting system according to an eighth embodiment of the present invention.

In FIG. 26, the leakage oil detecting system comprises, as like in the former embodiments, an irradiation apparatus 110, an observation apparatus 120, and a processor 130. The irradiation apparatus 110 comprises a pulse beam source 111, a lens 114 for throttling an irradiated pulse beam 112 and introducing it to an optical fiber 113, an optical fiber 113 for transmitting the introduced pulse beam 112 up to the vicinity of a monitoring region, and an irradiation head 115 for irradiating a purposed monitoring region with the pulse beam 112. The irradiation head 115 comprises an irradiation lens 112 for irradiating the monitoring region by enlarging the pulse beam 112 to the size of the monitoring region.

The observation apparatus 120 comprises an observation wavelength selection apparatus 155 for deciding the type of leakage oil, a lens 122 for adjusting a region to be observed to a monitoring region, a fast-gate-provided image intensifier 143 having fast-shutter function and image-intensifying function for selecting only the luminous period of oil to perform observation, an image fiber 144 for image-transmitting a detection image observed by the fast-gate-provided image intensifier 143, and a CCD camera 145 for monitor-displaying a transmitted detection image. Because the observation wavelength selection apparatus 155 is provided with a plurality of wavelength selection devices, the selection apparatus 155 is able to select observation wavelengths.

The processor 130 comprises a timing controller 131 for controlling the irradiation timing of the pulse beam source 111 and the shutter timing of the fast-gate-provided image intensifier 143 and selecting only the period in which oil fluoresces after irradiation of the pulse beam 112 to perform observation, a timing signal transmission line 132 for transmitting a timing signal from the timing controller 131 to the pulse beam source 111, a film thickness distribution computing apparatus 147 for computing the film thickness distribution of leakage oil by correcting the fluorescence intensity of oil in accordance with the information for the distance between a monitoring object and the oil detector, a type-of-oil decision apparatus 156 for deciding the type of leakage oil, an image monitor 149 for image-displaying the film thickness distribution obtained by the film thickness distribution computing apparatus 147 or the type of oil decided by the type-of-oil decision, apparatus 156, and an alarm 136 for communicating the presence or absence of oil leakage to persons.

It is assumed that the type of the leakage oil 139 to be detected is unknown and the oil 139 leaks from a unit under normal illumination by a fluorescent lamp or the like.

Functions and advantages of the eighth embodiment will be described below.

The type-of-oil decision apparatus 156 observes leakage oil with two types of observation wavelengths and decides the type of leakage oil in accordance with the fluorescence intensity ratio between the two wavelengths. This is because the fluorescence wavelength of oil is peculiar to the type of oil and therefore, the fact that the fluorescence intensity ratio shows a value inherent in the type of oil is used. For example, by obtaining the fluorescence intensity ratio between the observation wavelength 300 nm and the observation wavelength 400 nm which are defined by the following expression (16), it is possible to decide the type of oil because the fluorescence intensity ratio shows a value inherent in the type of oil as shown in Table 3. Moreover, it is possible to optionally select two observation wavelengths.

[Expression 16]

(Fluorescence intensity ratio)=(Fluorescence intensity of observation wavelength 400 nm/(Fluorescence intensity of observation wavelength 300 nm)     (16)

TABLE 3

| Fluorescence Intensity Ratios of Various Types of Oils (Observation Wavelengths of 300 and 400 nm) | |
| --- | --- |
| Type of Oil | Fluorescence Intensity Ratio |
| Gas turbine oil | 9.86 |
| Steam turbine oil | 0.62 |
| High-pressure hydraulic oil | 0.06 | observing the leakage oil with two types of observation wavelengths and obtaining the fluorescence intensity ratio between the two wavelengths, it is possible to decide the type of the leakage oil because the fluorescence intensity ratio shows a value inherent in the type of oil.

The oil detector of this embodiment is used to decide the type of the leakage oil 139 leaked from a unit under normal illumination by the fluorescent lamp or the like shown in FIG. 26. A pulse beam source 111 uses the fourth harmonic of a YAG laser (luminescence wavelength of 266 nm, pulse width of 5 ns: FWHM). By setting a luminescence wavelength to 266 nm, it is possible to excite every type of oil to be detected and make it luminesce. The pulse beam emitted from the pulse beam source 111 is throttled by the lens 114 and enters the optical fiber 113. The pulse beam is led to the irradiation head 115 by the optical fiber 113. The irradiation head 115 irradiates a monitoring region with the pulse beam by adjusting the pulse beam to an optional size in accordance with the size of the monitoring region. The leakage oil 139 absorbs the pulse beam emitted from the irradiation head 115 to emit fluorescence. Therefore, the observation wavelength of the observation wavelength selection apparatus 155 is first set to 300 nm and the fast-gate-provided image intensifier 143 of the observation apparatus 120 is operated by the timing controller 131 only for a period of 200 ns after irradiation of the pulse beam to observe a detection image with an observation wavelength of 300 nm. The detection image observed by the fast-gate-provided image intensifier 143 is image-transmitted to the image fiber 144 and picked up by the CCD camera 145. Thereafter, the detection image is sent to the processor 130. Then, the observation wavelength of the observation wavelength selection apparatus 155 is set to 400 nm and similarly, a detection image with an observation wavelength of 400 nm is observed and sent to the processor 130.

The processor 130 obtains a fluorescence intensity distribution I300(x,y) of the detection image with the observation wavelength of 300 nm by the film thickness distribution computing apparatus 147 and a fluorescence intensity distribution $I_{400}(x,y)$ of the next observation wavelength 400 nm and sends the distributions to the type-of-oil decision apparatus 156. The type-of-oil decision apparatus 156 obtains the fluorescence intensity ratio distribution R of the observation wavelengths 300 and 400 nm shown by the following expression (17) and decides the type of leakage oil at an oil leakage portion corresponding to a pixel (x,y) in accordance with the fluorescence intensity ratio distribution R(x,y) and Table 3.

[Expression 17]

$$R(x, y) = \frac{I_{400}(x, y)}{I_{300}(x, y)} \quad (17)$$

It is possible to successively display the decided type of leakage oil, detection image, fluorescence intensity distribution, and fluorescence intensity ratio distribution by the image monitor 149. A detection image in which only leakage oil fluoresces can be obtained by the image monitor 149 and moreover, early detection is realized because even a very small quantity of leakage oil can be detected when it fluoresces. Moreover, by selecting the fluorescence wavelength of the oil and perform observation only for the luminous period by the observation filter 121 and the fast-gate-provided image intensifier 143, it is possible to communicate the presence of the leakage oil and the type of the leakage oil to persons by turning on a warning lamp or outputting sounds by the alarm 136.

As the result of the above functions, by selecting the luminescence wavelength of oil and observing only the luminous period by the observation filter 121 and the fast-gate-provided image intensifier 143, it is possible to select and observe only the fluorescence of oil even if there is a disturbance by a fluorescent lamp or the like or luminescence of a background unit. Furthermore, by observing leakage oil with two types of observation wavelengths to obtain the fluorescence intensity ratio between the two observation wavelengths, it is possible to decide the type of leakage oil because the fluorescence intensity ratio shows a value inherent in the type of oil.

According to the third to eighth embodiments of the present invention, it makes possible to selectively detect the leakage oil by exciting an oil through irradiation of ultraviolet light to make the leakage oil luminesce and selecting the wavelength of the luminescence to perform observation only for the luminous period. Moreover, by applying signal processing or image processing to a detection result, it is possible to detect a very small quantity of foggy or thin-film leakage oil, decrease the frequency of erroneous detection due to the restriction of a detection place or detection atmosphere, a disturbance by a fluorescent lamp or the like, or deterioration of an apparatus, and specify the area, film thickness distribution, quantity, type, and portion of leakage oil.

It is to be noted that the present invention is not limited to the described embodiments and many other changes, modifications and combinations may be made without departing from the scopes of the appended claims.

We claim:

1. An oil detecting system for detecting a leakage oil by optical fluorescence measurement means even in the presence of external light, comprising:
    an irradiation apparatus for irradiating a pulsed light including an absorption wavelength of an oil to be detected and exciting molecules of the oil to make the oil fluoresce;
    a wavelength selection apparatus for selecting a fluorescence wavelength of the leakage oil fluoresced by the irradiation apparatus; and
    an observation apparatus operatively connected to the wavelength selection apparatus and including means for selecting a period of observing fluorescing of the leakage of oil after the pulsed light is irradiated by the irradiation apparatus.

2. An oil detecting system according to claim 1, wherein said irradiation apparatus comprises a pulse laser serving as is a pulse-beam irradiation apparatus.

3. An oil detecting system according to claim 1, wherein said wavelength selection apparatus comprises a band-pass filter.

4. An oil detecting system according to claim 1, wherein said observation apparatus comprises an image intensifier provided with fast-shutter function and image-intensifying function.

5. An oil detecting system according to claim 1, further comprising a processing apparatus operatively connected to the observation apparatus and adapted to process an image or a signal from the observation apparatus.

6. An oil detecting system according to claim 1, wherein said irradiation apparatus comprises a pulse-flash lamp.

7. An oil detecting system according to claim 6, wherein said wavelength selection apparatus comprises a band-pass filter.

8. An oil detecting system according to claim 6, wherein said observation apparatus comprises either one of photomultiplier combined with a boxcar integrator or fast-gate-function-provided photomultiplier.

9. An oil detecting system according to claim 6, further comprising a processing apparatus operatively connected to the observation apparatus and adapted to process an image or a signal from the observation apparatus.

10. An oil detecting system according to claim 1, wherein said time that the leakage oil fluoresces light is a fluorescing time of the leakage oil in a range at which the leakage oil has fluorescing strength more than that of another substance.

11. An oil detecting system for detecting an oil leakage by optical fluorescence measurement means even in the presence of external light, comprising:
    an irradiation apparatus for irradiating an oil to be detected with a pulse beam including an absorption wavelength of the oil and exciting molecules constituting the oil to make the oil fluoresce;

a wavelength selection apparatus for selecting a fluorescence wavelength of the oil excited by the irradiation apparatus;

an observation apparatus operatively connected to the wavelength selection apparatus and including means for selecting a period of fluorescing the leakage oil after the pulse beam is irradiated by the irradiation apparatus; and a processing apparatus operatively connected to the irradiation apparatus and the observation apparatus for performing image- or signal-processing to display an output of the observation apparatus.

12. An oil detecting system according to claim 11, wherein said irradiation apparatus comprises a pulse beam source and a wavelength selection device having a curved surface so as to emit an irradiation beam with a purposed wavelength in any direction.

13. An oil detecting system according to claim 11, wherein said observation apparatus is provided with a gate function and includes a light detection device for observing fluorescence of the oil and said processing apparatus includes a signal integration device for integrating detection signals of the leakage oil detected by the light detection device.

14. An oil detecting system according to claim 13, wherein said light detection device is a photomultiplier.

15. An oil detecting system according to claim 13, wherein said light detection device is an avalanche photodiode.

16. An oil detecting system according to claim 11, wherein said observation apparatus comprises an image intensifying tube provided with fast shutter function and image intensifying function and said processing apparatus includes an image integrating processor for integrating oil fluorescence detection images detected by the image intensifying tube.

17. An oil detecting system according to claim 11, wherein said processing apparatus includes an oil film computing device for computing a film thickness of the leakage oil.

18. An oil detecting system according to claim 17, wherein said film thickness computing device calculates the oil film thickness in accordance with the fluorescence intensity of the oil observed by said observation apparatus.

19. An oil detecting system according to claim 17, wherein said film thickness computing device performs an integration processing detection for signals of the leakage oil up to a constant value and assumes the oil film thickness in accordance with an integrated number of the integration processings.

20. An oil detecting system according to claim 11, wherein said irradiation apparatus includes an irradiation wavelength selection device adapted to adjust a film thickness range to be measured by changing an irradiation wavelength of the light beam from the irradiation apparatus.

21. An oil detecting system according to claim 11, wherein said irradiation apparatus includes a light-source deterioration correction device for correcting a film-thickness measurement accuracy by measuring irradiation intensity of the pulse beam.

22. An oil detecting apparatus according to claim 11, wherein said processing apparatus includes a film thickness distribution computing device for obtaining a fluorescence intensity distribution by correcting the fluorescence intensity of a detection image in accordance with an information of a distance from an object to be monitored to the observation apparatus and computing the film thickness distribution of the oil in accordance with the fluorescence intensity distribution.

23. An oil detecting system according to claim 20, wherein said observation apparatus includes an image intensifying tube provided with a fast shutter function and an image intensifying function and said processing apparatus includes an oil quantity computing device for obtaining an oil leakage quantity by extracting a fluorescent region of the oil from a detection image and using the fluorescent region and a film thickness computing result by the film-thickness computing device.

24. An oil detecting system according to claim 11, wherein said observation apparatus includes an image intensifying tube provided with a fast shutter function and an image intensifying function and said processing apparatus includes an oil leakage portion specifying device for specifying an oil leakage portion in accordance with a detection image of the oil scattered in form of foggy oil fine particles.

25. An oil detecting system according to claim 11, wherein said irradiation apparatus includes an irradiation head for irradiating the pulse beam to a monitoring area and a reflecting means attached to a front portion of the irradiation head with a predetermined distance.

26. An oil detecting system according to claim 11, wherein said observation apparatus includes an oil-type discrimination device for observing the oil by using more than two kinds of observation wavelength and discriminating a type of the oil in accordance with a fluorescence intensity ratio of the observed two kinds of the observation wavelength.

27. An oil detecting system according to claim 11, wherein said time that the leakage oil fluoresces light is a fluorescing time of the leakage oil in a range at which the leakage oil has fluorescing strength more than that of another substance.

* * * * *